United States Patent

Sousa et al.

Patent Number: 6,107,037
Date of Patent: Aug. 22, 2000

[54] METHODS FOR USING MUTANT RNA POLYMERASES WITH REDUCED DISCRIMINATION BETWEEN NON-CANONICAL AND CANONICAL NUCLEOSIDE TRIPHOSPHATES

[75] Inventors: Rui Sousa, San Antonia, Tex.; Jerome J. Jendrisak, Madison, Wis.

[73] Assignees: Epicentre Technologies Corporation, Madison, Wis.; The University of Texas, Ausin, Tex.

[21] Appl. No.: 09/100,803

[22] Filed: Jun. 19, 1998

Related U.S. Application Data

[62] Division of application No. 08/713,331, Sep. 13, 1996, Pat. No. 5,849,546.

[51] Int. Cl.[7] .............................. C12Q 1/68; C12P 19/34; C07H 21/04
[52] U.S. Cl. ................................. 435/6; 435/5; 435/91.2; 536/22.1; 536/24.3; 536/24.32
[58] Field of Search ..................... 435/6, 91.2; 536/22.1, 536/24.3, 24.32

[56] References Cited

U.S. PATENT DOCUMENTS

| | | | |
|---|---|---|---|
| 4,683,195 | 7/1987 | Mullis et al. | 435/6 |
| 5,075,216 | 12/1991 | Innis et al. | 435/6 |
| 5,622,824 | 4/1997 | Koster et al. | 435/6 |

OTHER PUBLICATIONS

Sousa et al, "A mutant T7 RNA polymerase as a DNA polymerase", The Embo Journal, vol. 14(18), pp. 4609–4621, 1995.

Kostyuk et al, "Mutants of T7 RNA polymerase that are able to synthesize both RNA and DNA", FEBS Letters, vol. 369, pp. 165–168, Jun. 13, 1995.

Axelrod et al, "Transcription from Bacteriophage T7 and SP6 RNA Polymerase Promoters in the Presence of 3–Deoxyribonucleoside 5–triphosphate Chain Terminators", Biochemistry, vol. 24, pp. 5716–5723, Mar. 15, 1995.

Stratagene catalog, p. 39, 1988.

"Probe Amplifier System Based on Chimeric Cycling Oligonucleotides," *Biotechniques* 9(2):142–146, 1990.

W.M. Barnes, "DNA Sequencing by Partial Ribosubstitution," *J. Mol. Biol.* 119:83–99, 1978.

E.T. Butler and M.J. Chamberlin, "Bacteriophage SP6–specific RNA Polymerase," *J. Biol. Chem.* 257 (10):5772–5778, 1982.

C. Cazenave, et al., "RNA template–directed RNA systhesis by T7 RNA polymerase," *PNAS* 91:6972–6976, 1994.

D.H. Jones and B.H. Howard, "A Rapid Method for Recombination and Site–Specific Mutagenesis by Placing Homologous Ends on DNA Using Polymerase Chain Reaction, " *Biotechniques* 10(1): 62–66, 1991.

G.A. Kassavetis, et al., "Bacteriophage SP6–specific RNA Polymerase, " *J. Biol. Chem.* 257(10)5779–5788, 1982.

(List continued on next page.)

*Primary Examiner*—Jeffrey Fredman
*Assistant Examiner*—Arun Chakrabarti
*Attorney, Agent, or Firm*—Quarles & Brady LLP

[57] ABSTRACT

A method for synthesizing a nucleic acid molecule comprising at least one non-canonical nucleoside triphosphate using a mutant polymerase having a reduced discrimination between canonical and non-canonical substrates is disclosed. The method comprises incubating a template nucleic acid in a reaction mixture comprising the mutant nucleic acid polymerase and the appropriate canonical and non-canonical nucleoside triphosphates which are desired substrates for the mutant nucleic acid polymerase. The present invention is also a method of determining the sequence of a nucleic acid molecule using the mutant polymerase to create a nucleic acid molecule comprising at least one non-canonical nucleoside triphosphate.

29 Claims, 8 Drawing Sheets

OTHER PUBLICATIONS

D.A. Kostyuk, et al., "Mutants of T7 RNA polymerase that are able to synthesize both RNA and DNA," *FEBS Letters* 369:165–168, 1995.

H. Kotani, et al., "Nucleotide sequence and expression of the cloned gene of bacteriophage SP6 RNA polymerase," *Nucl. Acids Res.* 15(6):2653–2664, 1987.

R. Sousa and R. Padilla, "A mutant T7 RNA polymerase as a DNA polymerase," *EMBO J.* 14(18):4609–4621, 1995.

E. Uhlmann, et al., "Antisense oligonucleotides: A new therapeutic principle," *Chem. Rev.* 90:543–593, 1990.

A. Wolfgang, et al., "Kinetic characterization of ribonuclease–resistant 2'–modified hammerhead ribozymes," *Science* 253:314–317, 1991.

# METHODS FOR USING MUTANT RNA POLYMERASES WITH REDUCED DISCRIMINATION BETWEEN NON-CANONICAL AND CANONICAL NUCLEOSIDE TRIPHOSPHATES

This is a division of application Ser. No. 08/713,331, Sep. 13, 1996, now U.S. Pat. No. 5,849,546.

FIELD OF INVENTION

The field of the present invention is methods for producing nucleic acid molecules containing at least one non-canonical nucleotide and for characterizing nucleic acid molecules by synthesizing nucleic acid molecules containing at least one non-canonical nucleotide in vitro using mutant nucleic acid polymerases having at least a 10-fold reduced discrimination between 2'-deoxyribonucleoside-5'-triphosphates and ribonucleoside-5'-triphosphates as substrates compared to the corresponding wild-type enzymes.

BACKGROUND

There are a number of procedures commonly used in the art for in vitro synthesis of nucleic acid molecules, including both DNA and RNA. For example, one may use an in vitro transcription reaction to synthesize RNA from a DNA template present in the reaction. T7-type RNA polymerases, such as T7 RNA polymerase, T3 RNA polymerase or SP6 RNA polymerase, are commonly used in such reactions, although many other RNA polymerases may also be used. Usually, but not always, synthesis of RNA is de novo (i.e., unprimed), and usually, but not always, transcription is initiated at a sequence in the template that is specifically recognized by the RNA polymerase, termed a "promoter" or a "promoter sequence". A method for in vitro transcription is presented herein.

Procedures for in vitro nucleic acid synthesis are also commonly used in the art to amplify nucleic acid molecules, including both DNA and RNA. For example, transcriptions using RNA polymerases are an integral part of "nucleic acid sequence-based amplification" (NASBA), "self-sustained sequence replication" (3SR), and "transcription-mediated amplification" (TMA) Hill, C. S., 1996, three similar methods for amplifying nucleic acid molecules in vitro.

By way of example, all or a specific portion of an RNA molecule may be amplified using NASBA (Compton, et al., 1991) or 3SR (Fahy, et al., 1991) by isothermal incubation of a sample RNA in a buffer containing two primers (a first primer complementary to the RNA molecule and encoding a promoter sequence for an RNA polymerase and a second primer complementary to the 3'-end of the first cDNA strand resulting from reverse transcription of the RNA molecule), an RNA- and DNA-dependent DNA polymerase which also has RNase H activity (or a separate RNase H enzyme), all four canonical 2'-deoxynucleoside-5'-triphosphates (dATP, dCTP, dGTP and dTTP), an RNA polymerase that recognizes the promoter sequence of the first primer, and all four canonical ribonucleoside-5'-triphosphates (rATP, rCTP, rGTP and rUTP).

A first cDNA strand is synthesized by extension of the first primer by reverse transcription. Then, the RNase H digests the RNA of the resulting DNA:RNA hybrid, and the second primer primes synthesis of the second cDNA strand. The RNA polymerase then transcribes the resultant double-stranded DNA (ds-DNA) molecule from the RNA polymerase promoter sequence, making many more copies of RNA, which in turn, are reversed transcribed into cDNA and the process begins all over again. This series of reactions, from ds-DNA through RNA intermediates to more ds-DNA, continues in a self-sustained way until reaction components are exhausted or the enzymes are inactivated. DNA samples can also be amplified by other variations of NASBA or 3SR or TMA.

Another nucleic acid amplification method involving DNA synthesis is the polymerase chain reaction (PCR).

By way of example, a specific portion of a DNA molecule may be amplified using PCR by temperature cycling of a sample DNA in a buffer containing two primers (one primer complementary to each of the DNA strands and which, together, flank the DNA sequence of interest), a thermostable DNA polymerase, and all four canonical 2'-deoxynucleoside-5'-triphosphates (dATP, dCTP, dGTP and dTTP). The specific nucleic acid sequence is geometrically amplified during each of about 30 cycles of denaturation (e.g., at 95° C.), annealing of the two primers (e.g., at 55° C.), and extension of the primers by the DNA polymerase (e.g., at 70° C.), so that up to about a billion copies of the nucleic acid sequence are obtained. RNA may be similarly amplified using one of several protocols for (reverse transcription-PCR) RT-PCR, such as, for example, by carrying out the reaction using a thermostable DNA polymerase which also has reverse transcriptase activity (Myers and Gelfand, 1991).

The polymerase chain reaction, discussed above, is the subject of numerous publications and patents, including, for example: Mullis, K. B., et al., U.S. Pat. No. 4,683,202 and U.S. Pat. No. 4,965,188.

A variety of procedures for using in vitro nucleic acid synthesis for characterizing nucleic acid molecules, including both DNA and RNA, also are known in the art.

There are many reasons for characterizing nucleic acid molecules. For example, genes are rapidly being identified and characterized which are causative or related to many human, animal and plant diseases. Even within any particular gene, numerous mutations are being identified that are responsible for particular pathological conditions. Thus, although many methods for detection of both known and unknown mutations have been developed (e.g., see Cotton, 1993), our growing knowledge of human and other genomes makes it increasingly important to develop new, better, and faster methods for characterizing nucleic acids. Besides diagnostic uses, improved methods for rapidly characterizing nucleic acids will also be useful in many other areas, including human forensics, paternity testing, animal and plant breeding, tissue typing, screening for smuggling of endangered species, and biological research.

One of the most informative ways to characterize a DNA molecule is to determine its nucleotide sequence. The most commonly used method for sequencing DNA at this time (Sanger, et al., 1977) uses a DNA polymerase to produce differently sized fragments depending on the positions (sequence) of the four bases (A=Adenine; C=Cytidine; G=Guanine; and T=Thymine) within the DNA to be sequenced. In this method, the DNA to be sequenced is used as a template for in vitro DNA synthesis. RNA may also be used as a template if a polymerase with RNA-directed DNA polymerase (i.e., reverse transcriptase) activity is used. In addition to all four of the deoxynucleotides (dATP, dCTP, dGTP and dTTP), a 2',3'-dideoxynucleotide is also included in each in vitro DNA synthesis reaction at a concentration that will result in random substitution of a small percentage of a normal nucleotide by the corresponding dideoxynucleotide. Thus, each DNA synthesis reaction yields a mixture of DNA fragments of different lengths corresponding to chain termination wherever the dideoxynucleotide was incorporated in place of the normal deoxynucleotide.

The DNA fragments are labelled, either radioactively or non-radioactively, by one of several methods known in the art and the label(s) may be incorporated into the DNA by extension of a labeled primer, or by incorporation of a labelled deoxy- or dideoxy- nucleotide. By carrying out DNA synthesis reactions for each of the four dideoxynucleotides (ddATP, ddCTP, ddGTP or ddTTP), then separating the products of each reaction in adjacent lanes of a denaturing polyacrylamide gel or in the same lane of a gel if different distinguishable labels are used for each reaction, and detecting those products by one of several methods, the sequence of the DNA template can be read directly. Radioactively-labelled products may be read by analyzing an exposed X-ray film. Alternatively, other methods commonly known in the art for detecting DNA molecules labelled with fluorescent, chemiluminescent or other non-radioactive moieties may be used.

Because 2',3'-dideoxynucleotides (ddNTPs), including even ddNTPs with modified nucleic acid bases, can be used as substrates for many DNA polymerases, Sanger's dideoxy-sequencing method is widely used. Recently, Tabor and Richardson (EP application 942034331, 1994) reported that mutations at specific sites in many DNA polymerases improved the ability of these mutant enzymes to accept ddNTPs as substrates, thereby leading to improved DNA polymerases for DNA sequencing using the Sanger method.

Nucleic acid sequencing provides the highest degree of certainty as to the identity of a particular nucleic acid. Also, nucleic acid sequencing permits one to detect mutations in a gene even if the site of the mutation is unknown. Sequencing data may even provide enough information to permit an estimation of the clinical significance of a particular mutation or of a variation in the sequence.

Cycle sequencing is a variation of Sanger sequencing that achieves a linear amplification of the sequencing signal by using a thermostable DNA polymerase and repeating chain terminating DNA synthesis during each of multiple rounds of denaturation of a template DNA (e.g., at 95° C.), annealing of a single primer oligonucleotide (e.g., at 55° C.), and extension of the primer (e.g., at 70° C.).

Other methods for sequencing nucleic acids are also known besides the Sanger method. For example, Barnes described a method for sequencing DNA by partial ribo-substitution (Barnes, W. M., 1977). In this method, a pre-labelled primer was extended in vitro on a template DNA to be sequenced in each of four reactions containing a wild-type DNA polymerase in the presence of Mn2+, all four canonical 2'-deoxyribonucleoside triphosphates, and one of four ribonucleoside triphosphates under deoxy-/ribonucleotide ratios and conditions that result in about 2% ribonucleotide substitution at each position. After alkali treatment to cleave the synthetic DNA at the positions of partial ribosubstitution, the sequence was determined by analyzing the fragments resulting from each reaction following electrophoresis on a denaturing polyacrylamide gel.

Although most methods for sequencing nucleic acids employ DNA polymerases, some work has also been reported on the use of T7 RNAP and SP6 RNAP for transcription sequencing of DNA templates beginning at the respective T7 or SP6 promoter sequence using 3'-deoxyribonucleoside-5'-triphosphates (Axelrod, V. D., and Kramer, F. R., 1985), and Q-Beta replicase for sequencing single-stranded RNA templates (Kramer, F. R., and Mills, D. R., 1978). Also, 3'-O-methyl-ribonucleoside-5'-triphosphates have been used for sequencing DNA templates with E. coli RNA polymerase ((Axelrod, V. D., et al., 1978). None of these techniques is commonly used at present, perhaps in part, due to the difficulty to obtain the 3'-deoxy- and 3'-O-methyl-nucleoside triphosphate substrates, while 2',3'-dideoxyribonucleoside-5'-triphosphates that are commercially available have not been found to be substrates for wild-type (w.t.) RNA polymerases.

In view of the numerous applications involving in vitro nucleic acid synthesis known in the art, it is useful to consider the properties of the key nucleic acid polymerase reagents which make these procedures possible, and which, if modified in their essential properties, might improve these procedures.

One classification of nucleic acid polymerases relies on their different template specificities (RNA or DNA), substrate specificities (rNTPs or dNTPs), and mode of initiation (de novo or primed). These designations usually refer to the template and substrate specificities displayed in vivo during the fulfillment of a polymerase's biological function.

In vitro, polymerases can display novel activities, albeit with reduced efficiency and/or under non-physiological conditions. E. coli DNA-directed DNA polymerase I, for example, can use RNA as a template, although there is a concomitant ~100-fold increase in dNTP $K_m$ (Ricchetti and Buc, 1993). T7 DNA-directed RNA polymerase can also use RNA as a template (Konarska and Sharp, 1989). These are not exceptional observations because it is a general property of polymerases that they display relaxed template specificity, at least in vitro.

While template specificity may be relaxed, polymerase substrate specificity is normally extremely stringent. T7 DNAP, for example, displays at least 2,000-fold selectivity for dNTPs over rNTPs, even in $Mn^{++}$ buffer which relaxes the ability of the polymerase to discriminate between dNTPs and ddNTPs (Tabor and Richardson, 1989).

It has been reported that transcripts synthesized by a T7 RNAP Y639F mutant in vivo yielded ½–⅓ of the protein per transcript compared to transcripts synthesized by the wild-type enzyme (Makarova, et al., 1995). The latter phenotype was unique to the Y639F mutant amongst a number of other active site mutants examined for in vivo expression, and indicated that Y639F transcripts contained a defect that led to their being inefficiently translated.

A polymerase with an altered substrate specificity would be useful in many molecular biological applications, such as creating a nucleic acid molecule comprising at least one non-canonical nucleotide.

SUMMARY OF THE INVENTION

We disclose herein the identification of mutant polymerases, such as T7-type RNAPs, that display the ability to use dNTPs. The mutations occur in tyrosine 639 within motif B (Delarue, et al., 1990) of T7 RNAP.

We have characterized the ability of the Y639 mutants, as well as a large number of other active site mutants, to use dNTPs in both $Mg^{++}$ and $Mn^{++}$ buffers. Our results point to a specialized role for tyrosine 639 in T7 RNAP—and the corresponding amino acid in other polymerases—in insuring that substrates to be added to the growing nucleic acid have the correct structure. The results reveal that both transcript and substrate structure affect the efficiency with which the transcript is extended and show that the restriction of unprimed initiation to RNA polymerases is not due to an intrinsic property of ribo- vs. deoxynucleotides, but simply to the selectivity of the polymerase active site. The present invention provides researchers with novel polymerase reagents and improved methods that expand the structural range of nucleic acids that can be enzymatically synthesized in vitro.

The present invention requires a polymerase with a reduced discrimination between canonical and non-canonical nucleoside triphosphates. In a preferred embodiment of the present invention, the polymerase has a reduced discrimination between rNTPs and dNTPs. In an especially preferred embodiment, the reduced discrimination is at least 10-fold compared to wild-type enzymes.

In one embodiment, the present invention is a method for synthesizing a nucleic acid molecule that comprises at least one non-canonical nucleotide. This method comprises the steps of incubating a template nucleic acid in a reaction mixture suitable for nucleic acid polymerization containing a mutant nucleic acid polymerase and the appropriate canonical and non-canonical nucleoside triphosphates which are substrates for a mutant nucleic acid polymerase and which are desired to be incorporated into the synthesized nucleic acid molecule.

In an especially preferred form of this method, the synthesized nucleic acid molecule has an altered susceptibility to a nuclease compared to a nucleic acid which could be synthesized using the corresponding non-mutant nucleic acid polymerase with canonical nucleoside triphosphates.

The present invention is also a method for determining the sequence of a nucleic acid molecule using a mutant RNA polymerase.

The method comprises synthesizing a nucleic acid molecule, either de novo from a promoter, or by extending a primer annealed to the template molecule in four separate reactions. The four separate reactions each have all 4 rNTPs and a portion of a ddNTP, or have all 4 dNTPs and a portion of a ddNTP, or have 4 2'-fluorine-substituted NTPs and a portion of a ddNTP. Chain termination will occur and the products may be evaluated so that the sequence of the template molecule may be deduced. In one embodiment of this method, the reactions which include a ddNTP occur in the same reaction mixture and are linked to a method for nucleic acid amplification, including, but not limited to, NASBA, 3SR, TMA, or other similar methods.

The present invention is also a partial ribo-substitution method for determining the sequence of a nucleic acid molecule. This method comprises synthesizing a nucleic acid molecule, either de novo from a promoter or by extending a primer annealed to the template molecule in four separate reactions. The reactions each have, either four dNTPs and a portion of an rNTP or four 2'-F-NTPs and a portion of an rNTP, or four different non-canonical nucleoside triphosphates, wherein these nucleoside triphosphates have substituents different than a hydroxyl group at the 2' position of the ribose and which the mutant polymerase can use as substrates for synthesis in nucleic acids, and a portion of an rNTP. The reaction products are then cleaved at sites containing an incorporated rNTP by using an alkaline solution or an RNase, and the cleaved nucleic acid fragments are separated according to size so that the sequence of the template molecule may be determined.

The present invention is also embodiments of a partial ribo-substitution method wherein the nucleic acid synthesis reactions of said method occur in the same reaction mixture and are also part of or linked to a method for nucleic acid amplification, including, but not limited to, NASBA, 3SR, TMA, or other similar methods.

In still other embodiments of the present invention, the products of either 1, 2, 3, or 4 of the dideoxy-sequencing reactions or of the partial ribo-substitution sequencing reactions are performed or analyzed to determine the presence or absence of a particular nucleic acid, or its relatedness to another nucleic acid, or whether it contains a mutation compared to another nucleic acid.

The present invention is also a kit for performing any of the above-identified methods.

It is an object of the present invention to provide a mutant polymerase capable of altered discrimination between canonical and non-canonical nucleoside triphosphates.

It is an object of the present invention to provide an improved DNA sequencing method.

It is an object of the present invention to provide a method to detect the presence of a nucleic acid.

It is an object of the present invention to provide a method to detect the identity of a nucleic acid.

It is an object of the present invention to provide a method to detect mutations in a nucleic acid.

It is an object of the present invention to minimize the steps involved in amplifying and sequencing, detecting, identifying and detecting mutations in nucleic acids.

It is another object of the present invention to provide a method for synthesizing nucleic acid molecules with altered nuclease susceptibility.

It is another object of the present invention to provide a method for synthesizing nucleic acid molecules comprising at least one non-canonical nucleoside triphosphate.

Other objects, features and advantages of the present invention will become apparent after examination of the specification, claims and drawings.

DESCRIPTION OF THE INVENTION

Definitions

Figure 1:
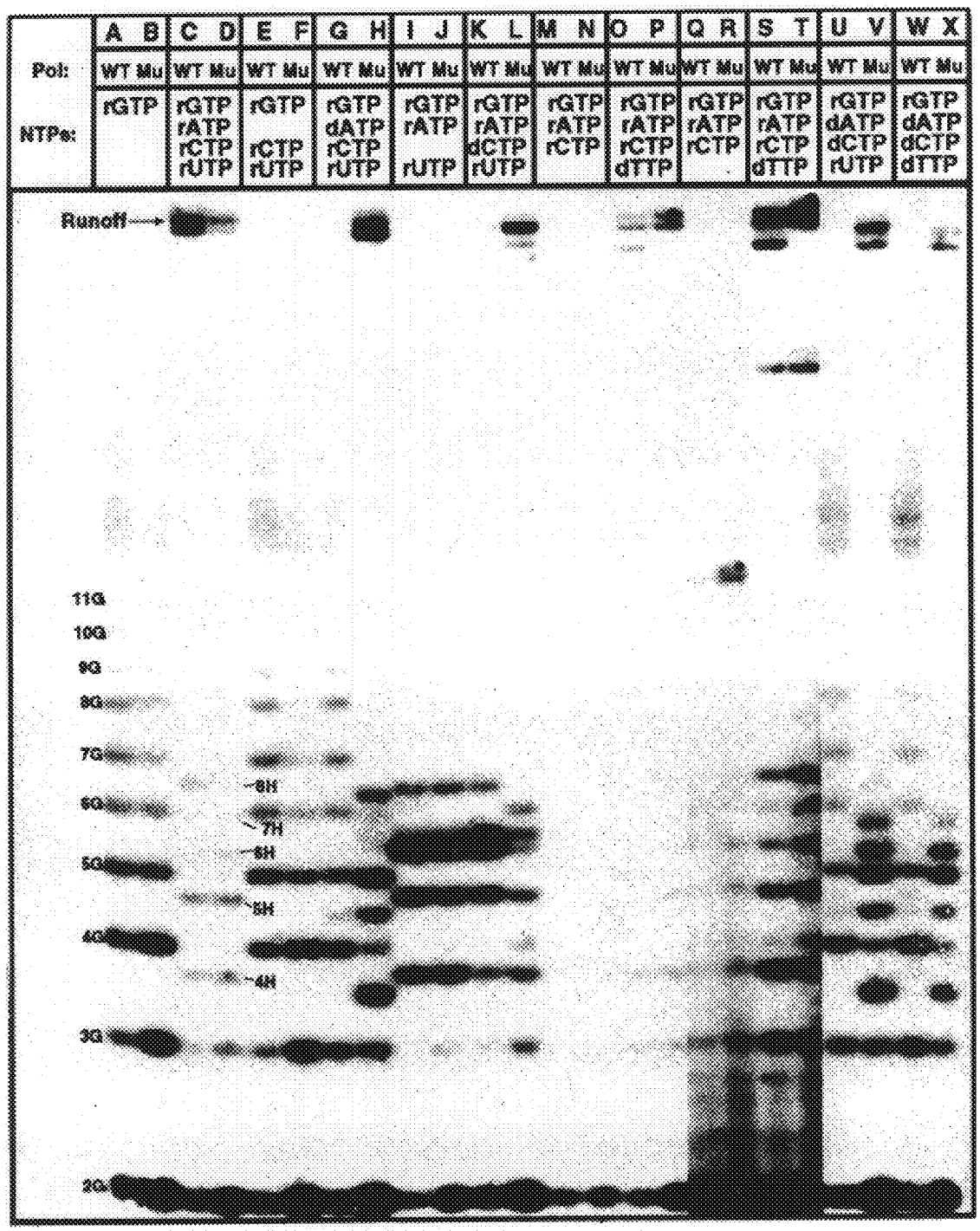
FIG. 1 diagrams the transcription products produced by Y639F and w.t. T7 RNAP in the presence of various combinations of rNTPs and dNTPs.

By "mutant polymerase" is meant a nucleic acid polymerase which has at least one altered amino acid compared to the corresponding wild-type polymerase, wherein said mutation or alteration results in the mutant polymerase having a reduced discrimination between non-canonical and canonical nucleoside triphosphates as substrates.

By "template" we mean a macromolecular pattern or mold for the synthesis of another macromolecule, composed of a sequence of nucleotides, either rNTPs or dNTPs, that serves to specify the nucleotide sequence of another structure.

"Nucleotide" refers to a base-sugar-phosphate compound. Nucleotides are the monomeric subunits of both types of nucleic acid polymers, RNA and DNA. "Nucleotide" refers to ribonucleoside triphosphates, rATP, rGTP, rUTP and rCTP, and deoxyribonucleoside triphosphates, such as dATP, dGTP, dTTP, dCTP.

As used herein, "nucleoside" refers to a base-sugar combination without a phosphate group. "Base" refers to the nitrogen-containing base, for example adenine (A), cytidine (C), guanine (G) and thymine (T) and uracil (U).

"Incorporation" refers to becoming a part of a nucleic acid polymer. There is a known flexibility in the terminology about incorporation of nucleic acid precursors. For example, the nucleotide dGTP is a deoxyribonucleoside triphosphate. Upon incorporation into DNA, it becomes a dGMP, or deoxyguanosine monophosphate moiety. Although there is no dGTP molecule in DNA, one may say that one incorporates dGTP into DNA.

As defined herein, a "canonical" nucleoside triphosphate for an RNA polymerase ("RNAP") consists of any ribonucleoside-5'-triphosphate ("rNTP" or "NTP") which has an hydroxyl group at the 2'-position of the sugar, including, but not limited to, the four common ribose-containing substrates for an RNA polymerase -ATP, CTP, GTP and UTP. A 2'-deoxyribonucleoside-5'-triphosphate ("dNTP") which has hydrogen at the 2'-position of the sugar, including, but not limited to, the four common deoxyribose-containing substrates (dATP, dCTP, dGTP and dTTP, also known as "TTP") for a DNA polymerase ("DNAP") is defined herein as a "non-canonical" nucleoside-5'-triphosphate or a "non-canonical NTP" or a "non-canonical nucleotide" or a "non-canonical deoxynucleotide" or a "non-canonical triphosphate" or a "non-canonical substrate" for an RNA polymerase. On the other hand, a "canonical" nucleoside triphosphate for a DNAP consists of any dNTP which has a hydrogen at the 2'-position of the sugar, while an rNTP is defined as a "non-canonical NTP" or a "non-canonical nucleotide" or a "non-canonical substrate" for a DNAP. The terms "canonical" and "non-canonical" are meant to be used herein only with reference to the 2' position of the sugar. Thus, as defined herein, 2',3'-dideoxynucleoside-5'-triphosphates ("2',3'-ddNTPs" or "ddNTPs") are "non-canonical" substrates for an RNAP, but are defined as "canonical" for a DNAP. Further, any other substituent than an hydroxyl group at the 2'-position of ribose or a hydrogen at the 2'-position of deoxyribose, including, but not limited to, a fluorine ("F" or "fluoro" group) or an amino group, would be defined as "non-canonical" for both RNAPs and DNAPs herein. The terms "canonical" or "non-canonical" also are not meant to refer to the nucleic acid bases attached to the sugar moieties. Thus, for example, other natural or modified nucleic acid bases attached to the 1'-position of ribose-5'-triphosphate would still be defined as "canonical" herein.

By "a (mutant) nucleic acid polymerase (enzyme) with reduced discrimination between canonical and non-canonical nucleoside triphosphate substrates", we have a specific quantitative definition calculated as follows:

1. One first determines the $K_m$ and the $k_{cat}$ for each enzyme (mutant and wild-type) using the non-canonical nucleotide as a substrate and using the canonical nucleotide as a substrate, as was described previously (Patra, et al., 1992). The value "$K_m$" expresses how readily the enzyme will bind the substrate (a larger $K_m$ implies weaker binding) and "$k_{cat}$" expresses the rapidity with which the substrate, once bound by the enzyme, is reacted upon.

2. One next calculates the numerical value for $k_{cat}/K_m$ for each enzyme and for each substrate. By broad scientific consensus, the specificity of an enzyme for a substrate is felt to be most suitably expressed by this ratio.

3. For each enzyme, one then calculates the numerical value obtained by using the value of $k_{cat}/K_m$ for the canonical substrate in the numerator and $k_{cat}/K_m$ for the non-canonical substrate in the denominator. This number indicates how much a given enzyme discriminates between the two substrates. For example, if this value equals 1, then the enzyme uses both the canonical and the non-canonical substrates equally well; it does not discriminate between the two substrates. If this value is greater than 1, then the enzyme discriminates by that factor between the two substrates; for example, if the value is 100, then the enzyme discriminates by a factor of 100 in favor of the canonical substrate compared to the non-canonical substrate. Similarly, a value less than 1 means that the enzyme discriminates in favor of the non-canonical substrate over the canonical substrate.

4. Finally, one compares the numerical value calculated in step 3 above for the wild-type (w.t.) enzyme with the value calculated in step 3 for the mutant enzyme. If the value calculated for the mutant enzyme is less than the value calculated for the wild-type enzyme, then the mutant enzyme "has a reduced discrimination for the non-canonical substrate compared to the wild-type enzyme." For example, if the values calculated in step 3 are 100 for the wild-type enzyme and 10 for the mutant enzyme, then the discrimination of the mutant enzyme in favor of the canonical substrate (or against the non-canonical substrate) is reduced 10-fold compared to the discrimination of the wild-type enzyme.

We have found that for wild-type T7 RNAP, the average of the $k_{cat}/K_m$ values for the four common rNTPs (ATP, CTP, GTP & UTP) is about 120-fold larger than the average $k_{cat}/K_m$ values for the four common dNTPs (dATP, dCTP, dGTP and dTTP); i.e., the wild-type enzyme discriminates by a factor of 120 for rNTPs vs. dNTPs. For the Y639F mutant enzyme, the average of the $k_{cat}/K_m$ values for the four common rNTPs is only about 6-fold larger than the average $k_{cat}/K_m$ values for the four common dNTPs. Thus, using the average $k_{cat}/K_m$ values for these substrates, the Y639F mutant T7 RNAP enzyme has about a 20-fold reduced discrimination between dNTPs and rNTPs. However, it is recognized that the difference in discrimination between wild-type and mutant enzymes will vary depending on the non-canonical substrates and the mutant enzymes used. Therefore, for the purposes of this invention, we herein define "a (mutant) nucleic acid polymerase (enzyme) with reduced discrimination between canonical and non-canonical nucleoside triphosphate substrates" as "a polymerase which has at least a 10-fold reduced discrimination compared to the corresponding wild-type enzyme for non-canonical nucleotides compared to canonical nucleotides, wherein the respective values for discrimination between canonical and non-canonical substrates is calculated using the average of the $k_{cat}/K_m$ values for all four rNTPs and all four dNTPs."

By "T7-type RNA polymerases" we mean T7, T3, φI, φIIH, W31, gh1, Y, A1122, SP6 and mitochondrial RNAPs.

In General

There are many reasons to synthesize nucleic acid molecules containing at least one non-canonical nucleotide. For example, incorporation of a non-canonical nucleotide may make the synthetic nucleic acid more resistant and therefore, more stable, to a nuclease, such as a ribonuclease. Also, one may wish to incorporate one or more non-canonical nucleotides which, for example, change the nuclease digestion pattern so that the product nucleic acid is easier to detect or characterize. For example, because RNase A cleaves RNA only after C or U, replacement of one or both of these rNMPs by a dNMP or other non-canonical nucleotide that is resistant to cleavage by RNase A would alter the digestion pattern of the nucleic acid.

There are many uses for nucleic acids which have one or more of these properties, such as nuclease resistance. For example, nucleic acids containing at least one non-canonical nucleotide may have advantages for use as ribozymes, or as nucleic acid molecules used for gene therapy, in a vaccine, in an antiviral composition, in an antimicrobial composition, in an anti-sense composition for regulating gene expression, in a composition for hybridization to a complementary nucleic acid, including as a primer, or as a probe for detection of a complementary nucleic acid for a variety of purposes.

Some nucleic acid molecules, such as those of mixed dNMP/rNMP composition, are highly useful for certain applications, but are presently difficult or impossible to produce on a practical scale. Thus, improved methods for synthesizing such nucleic acid molecules in vitro would be highly desirable. For example, probes of mixed DNA-RNA-DNA composition for the Cycling Probe Assay (Duck, P. G., et al., 1990) are currently made using difficult chemical methods.

We describe herein previously-unknown properties of T7-type RNA polymerases having a non-wild-type amino acid at specific positions within the polypeptides. We found that altering the amino acid at these specific positions results in mutant polymerases having at least a 10-fold reduced discrimination between 2'-deoxyribonucleoside-5'-triphosphates (dNTPs) and ribonucleoside-5'-triphosphates (rNTPs) as substrates in in vitro nucleic acid synthesis reactions compared to the corresponding wild-type enzymes. We found that these mutant polymerases also have reduced discrimination for other non-canonical nucleoside triphosphate (NTP) substrates, including 2',3'-dideoxy-ribonucleoside-5'-triphosphates (ddNTPs) and 2'-fluoro-nucleoside-5'-triphosphates (2'-F-NTPs). Based on knowledge of these novel properties, we have disclosed methods for using these mutant polymerases for producing nucleic acid molecules containing at least one non-canonical nucleotide and for characterizing nucleic acid molecules by synthesizing nucleic acid molecules containing at least one non-canonical nucleotide in vitro.

In one preferred embodiment, the invention uses mutant RNA polymerases that efficiently utilize deoxynucleoside triphosphates as substrates. In vitro, this mutant will synthesize RNA, DNA, or 'transcripts' of mixed dNMP/rNMP composition from a template molecule depending on the mix of NTPs or dNTPs present in the synthesis reaction.

Mutant Polymerases of the Present Invention

In a preferred embodiment, the polymerase mutation is conservative, for example, changing tyrosine 639 (of T7 polymerase) within the active site to phenylalanine, and does not substantially affect promoter specificity or overall activity. Non-conservative mutations of this tyrosine also reduce discrimination between deoxy- and ribonucleoside triphosphates, but these mutations also typically cause large activity reductions. Among the most active of the non-conservative mutations, enzymes with methionine or leucine in place of the wild-type tyrosine at the 639 position of T7 RNAP had about half the enzymatic activity of the wild-type enzyme.

Of 26 other mutations of other amino acid positions examined in and around the active site of T7 RNAP, none showed marked effects on rNTP/dNTP discrimination.

T7 RNA polymerase can use RNA templates as well as DNA templates and is capable of both primer extension and de novo initiation. The Y639F mutant, described below in the Examples, retains the ability to use RNA or DNA templates. Thus, this mutant can display de novo initiated or primed DNA directed DNA polymerase, reverse transcriptase, RNA directed RNA polymerase, or DNA directed RNA polymerase activities depending on the templates and substrates presented to it in the synthesis reaction.

A major theme of research on nucleic acid polymerases over the past several years has been the discovery of extensive structural similarity between the majority of these enzymes, even those from functionally different classes (Sousa, et al., 1993; Pelletier, et al., 1994; Jacob-Molina, et al., 1993; Kohlstaedt, et al., 1992; Sawaya, et al., 1994; Steitz, et al., 1994). One part of this work has been the identification of well-conserved residues. Five amino acids have been identified as invariant in a large number of DNA-directed RNA polymerases (Delarue, et al., 1990). In T7 RNAP these are D537, K631, Y639, G640A and D812. A specific, conserved function has been revealed for the two invariant aspartates in coordinating the catalytic $Mg^{++}$ ion (Sousa, et al., 1993; Pelletier, et al., 1994; Jacob-Molina, et al., 1993; Kohlstaedt, et al., 1993; Sawaya, et al., 1994; Steitz, et al., 1994). Our observations imply a similarly specific and conserved function for Y639 as a sensor of inappropriate geometry or structure in the template-NTP-primer/RNA complex.

The present invention encompasses methods for synthesis of nucleic acids containing at least one non-canonical nucleotide using mutant nucleic acid polymerases which have reduced discrimination for non-canonical nucleoside triphosphate substrates. The examples below demonstrate the reduced dNTP/rNTP discrimination of mutants of T7 RNA polymerase and SP6 RNA polymerase. Genes for other polymerases may be modified or mutated to obtain mutant enzymes which have similar reduced discrimination for non-canonical substrates. If one wished to mutate an RNA polymerase to have the properties described herein, one would first locate the amino acid corresponding to the T7 polymerase Y639 in other RNA polymerases. Identification of the corresponding mutation site in other polymerases can be done by the well-established procedure of sequence alignment, which involves aligning the amino acid sequences of two proteins, introducing gaps and insertions, and shifting the sequences with respect to each other while maintaining their original linearity. Such alignment procedures are often performed with the aid of one or more computer programs into which the amino acid sequences that one wishes to compare have been entered. When the sequence identity of two proteins is high enough (greater than or equal to 30%) over a sufficient length of amino acids (greater than or equal to 50), this procedure is very reliable in identifying amino acids that occupy corresponding structural and functional positions in the two proteins. Such conditions are met for the T7-type group of RNAPs, which include T7, T3, φI, φIIH, W31, gh1, Y, A1122, SP6 and mitochondrial RNAPs, and allow identification of the mutation site corresponding to Y639 in T7 RNAP.

Using this method, we predicted that the amino acid in w.t. SP6 RNAP that corresponded to the Y639 site in T7 RNAP was Y631, and as described herein, mutagenesis of this site resulted in a Y631F mutant SP6 RNAP which has a similar reduced discrimination for dNTPs compared to rNTPs like the Y639F mutant T7 RNAP.

From alignment studies, it is known that there is a conserved motif present in T7-like RNAPs and class I DNAPs with the following consensus sequences:

... K ... Y G ..

where Y is the tyrosine at amino acid number 639 in the T7 RNA polymerase protein. The same consensus sequence is observed in the SP6 RNA polymerase and T3 RNA polymerase proteins where a K (K=lysine) is succeeded by 7 amino acids and a Y G (G=glycine). In SP6 RNA polymerase the Y is at amino acid number 631 in the polypeptide chain, and in T3 RNA polymerase it is at amino acid number 573. By mutating the codon for Y631 in SP6 RNA polymerase such that a phenylalanine is at this position, the expected phenotypic change was realized.

In summary, one may locate the corresponding mutation site in other RNAPs by aligning the amino acid sequence of a T7-like RNAP, chosen from among T7, T3, φI, φIIH, W31, gh1, Y, A1122, SP6 and mitochondrial RNAPs, against the conserved motif given above and identifying which position corresponds to the Y639 position in T7 RNAP.

As stated above, the conserved motif is also present in class I DNAPs. While a structure of T7 RNAP complexed with NTP is not available, the structure of the homologous Klenow fragment of DNAP I with dNTP has been obtained (Beese, et al., 1993). This structure demonstrated that the amino acids encompassed within the above-mentioned conserved motif (i.e., amino acid residues 758 to 767 of $E.$ $coli$ DNAP I) are in proximity to the deoxyribose sugar of the dNTP, so that it is reasonable that mutations within this motif might affect the ability of a DNAP to discriminate between dNTPs and rNTPs. However, one of the present inventors found that when a mutation was made which changed the amino acid at the position in a class I DNAP corresponding to the Y639 mutation in T7 RNAP, the mutant DNAP retained enzymatic activity, but did not have a reduced discrimination for rNTPs compared to dNTPs. Thus, it is not obvious what mutations, if any, would result in a class I DNAP having reduced discrimination for rNTPs vs. dNTPs, even if it is reasonable to assume that such a mutation would occur within the above-mentioned conserved motif (residues 758 to 767 of $E.$ $coli$ DNAP I) which the structure shows to be in proximity to the dNTP.

Because the structure of the Klenow fragment of DNAP I complexed with dNTP was determined (Beese, et al., 1993), researchers have believed that the homologous conserved motif of T7 RNAP (i.e., amino acid residues 631–640) is likely to be in proximity to the ribose moiety of an NTP, as the case for the DNAP I. Nevertheless, prior to the work of the present invention, it was not possible to know which mutation, if any, might result in a reduced discrimination for dNTPs vs. rNTPs. Since the Y639 mutation of T7 RNAP was identified, as presented herein, one of the present inventors has modeled NTP in T7 RNAP (Huang, et al., submitted for publication) based on the structures of the homologous Klenow fragment of DNAP I complexed with dNTP (Beese, et al., 1993) and of RT complexed with primer-template (Jacabo-Molina, et al., 1993). Models based on either structure agree in placing the ribose close to Y639, and in revealing no other side chain capable of discriminating the hydrogen bonding character of the 2'-substituent within 5 angstroms of the 2'-group of the NTP. Thus, the model is consistent with our results related to a reduced discrimination of Y639 RNAP mutants for dNTPs vs. rNTPs, even though additional studies (Huang, et al., submitted for publication) have determined that the hydrogen bonding character is not the only factor involved in dNTP/rNTP discrimination.

Less is known about non-T7-type RNAPs. For many, the amino acid sequences are not known. Non-phage-encoded host bacterial RNA polymerases are complex multi-subunit proteins. A nucleotide polymerization site has been localized in the β subunit of $E.$ $coli$ RNA polymerase although participation of other subunits is not ruled out. In order to determine the site in a non-T7-like RNAP which would result in a reduced dNTP/rNTP discrimination, one would first use the above-described procedure of alignment to determine if the ... K Y G ... motif was present. If so, it may be possible to obtain the desired mutation in the same manner as for T7-like RNAPs. However, if the conserved motif is not present, one may obtain the desired mutation with greater difficulty by random mutagenesis and enzyme assay screening in order to find a change or changes that result in reduced dNTP/rNTP discrimination.

Once one has determined where the corresponding Y639 site is in the polymerase one wishes to mutate, one would use standard methods in the art of molecular biology to create an amino acid substitution. As disclosed above, a conservative substitution is preferable. For example, a substitution of a phenylalanine for a tyrosine is most preferable. The Examples below disclose a method for creating a mutant polymerase, but one of skill in the art will realize that there are many substitute methods of equal effectiveness.

Methods of the Present Invention

In one embodiment, the present invention is a method for using a mutant polymerase for synthesizing in vitro a nucleic acid molecule which comprises at least one non-canonical nucleotide in place of at least a portion of the canonical nucleotides. The method comprises the steps of incubating a template nucleic acid in a reaction mixture containing a mutant nucleic acid polymerase which has reduced discrimination between canonical and non-canonical nucleoside triphosphates, including between dNTPs and rNTPs, and the appropriate canonical or non-canonical nucleoside triphosphates which are substrates for the nucleic acid polymerase. One then follows standard polymerase reaction protocols and creates the synthesized nucleic acid molecule.

Preferably, the reactions also contain inorganic pyrophosphatase, which is known to increase the yields in in vitro transcription reactions (Cunningham, P. R. and Ofengand, J., 1990) and to reduce pyrophosphorolysis in in vitro DNA synthesis reactions (Tabor, S., and Richardson, C. C., 1990), as well as buffers and other components which are known to those of skill in the art to be optimal for the particular w.t. polymerase used. Cunningham and Ofengand (1990) provide an example of conditions which may be used for unprimed synthesis with T7 RNA polymerase or mutant T7 RNAPs, although one of skill in the art will recognize, with respect to reactions with these enzymes or other enzymes, the need to optimize the concentrations and ratios of canonical and non-canonical NTP substrates according to the respective $K_m$ and application and to modify reaction conditions, such as temperature, amount of enzyme, salt concentration, or divalent cation (e.g., Mg2+ or Mn2+) concentration, in order to produce improved results such as higher yield or a greater percentage of full-length products.

In a preferred form of this method, the resulting synthesized nucleic acid molecule has a different susceptibility to a nuclease compared to a nucleic acid synthesized by the corresponding non-mutant nucleic acid polymerase under identical reaction conditions with canonical substrates. By "different susceptibility" we mean to include reduced, increased, or, in the case of synthetic nucleic acids containing both canonical and non-canonical nucleotides, altered susceptibility to a nuclease, which may be either a DNAse or RNAse. The nature of the reduced, increased or altered susceptibility to a nuclease is also related to the properties of the nuclease. For example, a nucleic acid resistant to RNase A, which cleaves RNA only after C or U, may be synthesized using fewer non-canonical nucleotides (e.g., dNTPs or 2'-F-NTPs) than a nucleic acid which is resistant to RNase I, which cleaves after every base.

In a preferred form of the present invention, the resulting synthesized nucleic acid is a ribozyme or a nucleic acid molecule used for gene therapy, in a vaccine as an antiviral composition, in an antimicrobial composition, as an antisense composition for regulating gene expression, in a composition for hybridization to a complementary nucleic acid, such as for a primer, or as a probe for detection of a complementary nucleic acid.

The resulting synthesized nucleic acid may be either single- or double-stranded.

The present invention is also a kit for performing the method of synthesizing a nucleic acid containing at least one non-canonical nucleotide. Typically, the kit contains a mutant nucleic acid polymerase with a reduced discrimination for non-canonical compared to canonical substrates and data or information describing conditions under which the method may be performed.

The present invention is also improved methods for sequencing nucleic acids using a mutant nucleic acid polymerase of the present invention.

Because 2',3'-dideoxynucleotides are not substrates for wild-type RNA polymerase, it previously has not been possible to use the Sanger method for determining the sequence of a nucleic acid with an RNA polymerase, although 3'-deoxy- or 3'-hydroxymethyl analogs have been used as terminators for Sanger-like sequencing with RNA polymerases.

However, 2',3'-ddNTPs are substrates for the mutant nucleic acid polymerases of this invention which can also utilize both rNTPs and dNTPs as substrates, and the present invention is also a method for sequencing nucleic acid molecules (DNA or RNA) using a mutant nucleic acid polymerase and 2',3'-ddNTPs as terminators.

In one embodiment of this method, the nucleic acid to be sequenced, whether DNA or RNA, is used as a template for in vitro nucleic acid synthesis from a primer (i.e., primed synthesis) using a mutant RNA polymerase which has a reduced discrimination for dNTPs compared to rNTPs. Each of four different reactions also contains an amount of at least one nucleoside triphosphate corresponding to each nucleic acid base represented in either DNA or RNA, chosen from among the 2'-deoxynucleotides dATP, dCTP, dGTP and dTTP or dUTP, or the four common ribonucleotides ATP, CTP, GTP and UTP, or the 2'-fluorine-substituted nucleotides 2'-F-ATP, 2'-F-CTP, 2'-F-GTP and 2'-F-UTP or 2'-F-TTP. A 2',3'-dideoxynucleotide is also included in each in vitro nucleic acid synthesis reaction in an amount that will result in random substitution by the dideoxynucleotide of a small percentage of the corresponding rNTP, dNTP or 2'-F-NTP that is present in the reaction and that would be incorporated into the synthetic nucleic acid in a template-dependent fashion.

Thus, each DNA synthesis reaction yields a mixture of DNA fragments of different lengths corresponding to chain termination wherever the dideoxynucleotide was incorporated in place of the ribo-, 2'-deoxy- or 2'-fluoro- nucleotide. The DNA fragments are labelled, either radioactively or non-radioactively, by one of several methods known in the art and the label(s) may be incorporated into the DNA by extension of a labelled primer, or by incorporation of a labelled ribo-, deoxy-, 2'-fluoro- or 2',3'-dideoxynucleotide.

By carrying out DNA synthesis reactions for each of the dideoxynucleotides (ddATP, ddCTP, ddGTP and ddTTP or ddUTP), then separating the products of each reaction in adjacent lanes of a denaturing polyacrylamide gel or in the same lane of the gel if different distinguishable labels are used for each separate reaction, and then detecting those products by one of several radioactive or non-radioactive methods known in the art, the sequence of the DNA template can be read directly. Also, other matrices than polyacrylamide which separate the fragments based on size may be used. Those with skill in the art will also recognize that other nucleotide analogs generally used for reducing sequencing compressions, such as ribo-, deoxy- or 2'-fluoro- nucleoside triphosphates containing 7-deaza-guanine or inosine, may also be used in place of the ribo-, deoxy- or 2'-fluoro-nucleotide for which the respective analog is used.

The present invention also comprises another embodiment of this method for sequencing using 2',3'-ddNTPs and a mutant RNA polymerase which has a reduced discrimination for dNTPs compared to rNTPs. In this embodiment of the method, the nucleic acid to be sequenced, whether DNA or RNA, is used as a template for de novo (i.e., unprimed) in vitro nucleic acid synthesis beginning at an RNA polymerase promoter. In this embodiment, a primer is omitted from the reactions and depending on the promoter sequence, in addition to the other components used in the first embodiment, an amount of a dinucleoside tetraphosphate or a trinucleoside penta-phosphate may be added as an initiating nucleotide (Moroney and Piccirilli, 1991) so that the majority of nucleic acid synthesis is initiated from a single site. Because no primer is used, the labelling of the sequencing products must be carried out by one of the other methods envisioned and discussed with respect to the first embodiment of the method or by incorporating a label into or on an initiating dinucleotide or trinucleotide. In other respects, the second embodiment of this sequencing method of the invention is similar to the first embodiment of the method.

The present invention also comprises methods of sequencing nucleic acids by part al ribo-substitution using mutant nucleic acid polymerase which have a reduced discrimination between non-canonical and canonical nucleotides. These methods have advantages over the partial ribo-substitution sequencing method described by Barnes (1977), which relied on the use of a Mn2+-containing reaction buffer to relax the ability of a wild-type DNA polymerase to discriminate between dNTPs and rNTPs. Further, only DNA was used as a template for this method and de novo (i.e., unprimed) nucleic acid synthesis was not envisioned. In contrast, the ribo-substitution sequencing method of the present invention uses a mutant nucleic acid polymerase which has an inherent reduced discrimination between dNTPs and rNTPs and, although it may be included, Mn2+ is not required in the sequencing reactions. In still another embodiment, 2'-fluorine-substituted NTPs are used in place of dNTPs in the ribo-substitution reaction. Embodiments of the method of the present invention also include sequencing using either DNA or RNA as templates and sequencing using either nucleic acid primers or de novo nucleic acid synthesis from an RNA polymerase promoter sequence.

Since incorporation of the sequence-delimiting ribonucleotide does not terminate nucleic acid synthesis during partial ribo-substitution sequencing, all of the radioactive or non-radioactive label must be incorporated into the sequencing reaction products prior to incorporation of the first ribonucleotide in order to avoid multiple labeled produced from each nucleic acid molecule synthesized. Multiple labeled products, starting from different positions on the template, would make it difficult or impossible to interpret sequence results. Thus, labeling of nucleic acid products for partial ribo-substitution sequencing must be accomplished by means such as incorporating the label into a primer, when used, or into an initiating di- or tri- nucleotide, or by prelabelling in the presence of an amount of a labeled nucleotide which will be used up or destroyed and/or limiting 2'-deoxy- or 2'-fluoro-nucleotides prior to addition of the sequence-delimiting rNTPs.

We envision sequencing reactions wherein all of the distinguishable non-radioactive labels in, or attached to, or connected with, the products from more than one of the reactions, up to and including all four of the sequencing reactions for a template, or even reactions from multiple templates if distinguishable non-radioactive labels are present, are detected in or from a single lane of a sequencing gel or a single capillary electrophoresis tube or a single matrix or means of any kind using an automated sequencer or other detection device.

EXAMPLE

Example 1: Creation and Characterization of a Mutant T7 RNA Polymerase

A. Materials and Methods

Nucleic acids and NTPs: Nucleotides were from Pharmacia or USB/Amersham. Polynucleotides were from Pharmacia and the Midland Certified Reagent Company. Synthetic DNAs were prepared at the UTHSCSA DNA synthesis facility on an Applied Biosystems DNA synthesizer and purified by HPLC. A synthetic RNA 12mer was from the Midland Certified Reagent Company. Plasmids pT75 (Tabor and Richardson, 1985) and pBS (Stratagene Inc.) were purified from E. coli by alkaline-lysis and cesium chloride gradient centrifugation (Sambrook, et al., 1989). Radioactive nucleotides were from NEN Dupont or ICN.

Preparation and purification of mutant polymerases: Construction, expression, and purification of the T7 RNAP mutants was described previously (Bonner, et al., 1992).

Transcription reactions: Transcription reactions were carried out in 40 mM Tris-Cl pH 8.0, 15 MM $MgCl_2$, and 5 mM DTT or 20 mM Manganese Citrate pH 8.0, 5 mM DTT at 37° C. Template, polymerase, and NTP concentrations were as indicated in the legends to the figures and tables. Relative activity determinations were made by taking 4 μl aliquots of reactions at 5, 10, and 20 minute time points and spotting on to DE81 filter paper. Unincorporated nucleotides were separated from incorporated nucleotides by washing the filter paper with 0.5 M $KH_2PO_4$ pH 7.0 and retained radioactive nucleotide was quantitated with a Molecular Dynamics phosphorimager. Radioactive NTPs used were as indicated in figure and table legends. To evaluate rNTP/dNTP selectivity, reactions were run with 4 rNTPs and pT75 as template and α-$P^{32}$ rNTPs or α-$P^{32}$ dNTPs were used to label the transcripts. The relative rate of incorporation of an rNTP vs. its cognate dNTP was determined from the relative percentages of labeled rNTP vs. dNTP incorporated into DE81 retainable RNA at 5, 10, and 20 minute time points. Apparent miscoding frequencies were determined similarly, though in this instance the template was a single-stranded homopolymer and the reaction contained the complementary unlabeled rNTP, and complementary α-$P^{32}$ rNTP or one of the 3 non-complementary α-$P^{32}$ rNTPs. The relative percentages of labeled complementary vs. non-complementary rNTPs incorporated at 5, 10 and 20 minute time points gave an apparent miscoding rate. The rNTP/dNTP selectivity assay was used to test the following T7 RNAP mutants for effects on substrate discrimination: D537S, D537E, S539A, R551S, D552S, R627S, K631S, L637A, Y639S, Y639F, Y639A, G640A, F644A, G645A, Q649S, H810S, H811S, H811A, D812A, D812E, D812S, D812N, D879E+ΔF882+ΔA883, D879E+A881T+ΔA883, D879E+F884+A885, D879E+F882Y, D879E+ΔA883, D879E+F882W, D879E.

Elongation rate determinations were carried out as described (Golomb & Chamberlin, 1974) with some variations (Bonner, et al., 1994).

Determination of NTP $K_m$ and $k_{cat}$ was as described previously (Patra, et al., 1992).

B. Results

Structure of the transcripts synthesized by Y639F and the w.t. enzyme with rNTPs and dNTPS: FIG. 1 diagrams the structure of transcription products produced by Y639F and w.t. T7 RNAP in the presence of various combinations of rNTPs and dNTPs. The template was pT75 (Tabor and Richardson, 1985) cut with HindIII so that transcription from its T7 promoter generates a 59-base run-off transcript. Electrophoresis was on a 20% polyacrylamide 6M urea gel. Plasmid and polymerases were at concentrations of $10^{-7}$ M, and NTP concentrations were 0.5 mM (all rNTPs and dTTP), 1 mM (dATP, dGTP), or 5 mM (dCTP). γ-$P^{32}$-GTP was added to radiolabel the transcription products. Wild-type (WT) or Y639F mutant (Mu) polymerases and NTPs used are as indicated. Poly-rG products of various sizes are labeled in lane A ("2G", "3G", etc . . . ) and heterogeneous sequence abortive transcripts of different lengths are indicated by "4H", "5H", etc . . . in lane c. Lanes q–t are a 10-fold longer exposure of lanes m–p.

FIG. 1 shows transcription reactions carried out with the w.t. enzyme or the Y639F mutant polymerase and a T7 φ-10 promoter template. Transcription by T7 RNA polymerase, like other RNA polymerases, is characterized by an initial, poorly processive 'abortive' phase of transcription during which the short, nascent transcript frequently dissociates from the ternary complex. When the transcript reaches a length of ~9 bases transcription becomes highly processive and the transcript becomes stably associated with the elongation complex. On this promoter, which initiates with GGGAGACCGGAAU (SEQ ID NO:1), T7 RNAP can also synthesize long poly-G ladders (labeled "2G", 3G", etc. in lanes a and b) when rGTP is the sole NTP present (Martin, et al., 1988). Lanes c and d of the electrophoretic gel display the transcription products typical of runoff reactions counting all 4 rNTPs: there are abortive transcripts ranging up to 8 bases in length and a 59-base runoff product. The 4mer length the sequences of the poly-G transcripts and the abortive transcripts made in the presence of all 4 rNTPs (labeled "4H", "5H", etc.) diverge and no longer co-migrate with the poly-G transcripts of equivalent size.

When rATP is omitted from the transcription reactions (lanes e and f) normal elongation of the initially synthesized GGG trimer cannot occur. There are no heterogeneous sequence abortive transcripts or 59 base runoff products made and instead long poly-G transcript s, as in lane a, are made. Adding dATP to reactions lacking rATP does not change the transcripts produced by the w.t. enzyme (lane g). However, with the mutant enzyme we observed that addition of dATP (lane h) allows synthesis a long runoff transcript as well as synthesis of heterogenous sequence abortive transcripts that do not co-migrate with the poly-G transcripts. Observation of an abortive transcript in lane h running near the position of the "4H" band in lane d confirms extension of the GGG trimer with an A but note that the major 4mer transcript in lane h migrates close to, but not precisely with, the major 4mer in lane d or in adjacent lane i. This is consistent with the expectation that these 4mers will have identical sequence and length but different structure (i.e., rGrGrGrA in lanes d or i; rGrGrGdA in lane h). It should also be noted that some poly-G transcript synthesis is observed in lane h. For example, in lane h we observe both a heterogeneous sequence 4mer migrating near the "4H" position and a smaller amount of 4mer band migrating at the "4G" position. When 4 rNTPs are present (lanes c or d) the synthesis of poly-G transcripts is more completely suppressed. This indicates that dATP is utilized by Y639F, but not as efficiently as rATP.

When rCTP is omitted from the reaction, transcripts terminate predominately at the 6mer length because rCMP is normally first incorporated at position 7 (lanes i, j). Addition of dCTP does not allow extension of the 6mer in reactions with the w.t. enzyme (lane k). However, addition of dCTP to reactions with Y639F allows extension beyond the 6mer length and synthesis of the runoff transcript (lane 1). Again, the following should be noted: 1. The transcripts larger than 6 bases do not co-migrate with their counterparts in lanes c or d consistent with the expected structural difference despite length and sequence identity, 2. there is more termination at the 6- and 7mer points in lane 1 than in lanes c or d, indicating that Y639F uses dCTP well, but not as efficiently as it utilizes rCTP.

In lanes m and n UTP was omitted from the reactions. Lanes q–t show a 10-fold longer exposure of lanes m–p. Within the set of 4 NTPs, UTP is unique on this template since it first becomes incorporated into the transcript at the 13 base position. This corresponds to a transcript length subsequent to the transition form abortive to processive transcription. As a consequence of this transition, the ternary complex becomes more stable (Martin, et al., 1988). Therefore, when transcript extension is blocked during the processive phase of transcription, the stalled ternary complex does not rapidly dissociate (Shi, et al., 1988). Instead it remains stalled on the template, near the promoter, and blocks reinitiation. For this reason we observe a large decrease in the overall amount of transcription when UTP is omitted from the reaction in lanes m and n.

A longer exposure of lanes m and n (lanes q, r) does, however, reveal transcription products of the expected structure. When TTP is added to these reactions (lanes o, p, s, t) synthesis of the 59 base runoff transcript is observed with both the w.t. and Y639F mutant.

The ability of the w.t. enzyme to extend transcripts with TTP when it is unable to extend transcripts with the other dNTPs is also likely to be related to unique position at which UTP/TTP first becomes incorporated into the transcript. The amount of transcript termination or extension that occurs with a particular dNTP depends simply on the relative rates of ternary complex dissociation or dNMP incorporation (McClure and Chow, 1980). During abortive transcription complex, dissociation must be more rapid than the rate at which the w.t. enzyme incorporates dNMPs into its transcripts. During processive transcription even the expected slow rate of dNMP incorporation by the w.t. enzyme must be competitive with the slow rate of dissociation of the stable elongation complex, and an ability of the w.t. enzyme to incorporate dNMPs becomes manifest. Because elongation during the processive phase of transcription is fast (~230 bases/sec, Golomb and Chamberlin, 1974), while initiation and progression through abortive transcription is slow (Martin and Coleman, 1987; Martin, et al., 1988), elongation of the transcript from 11 to 59 bases is expected to contribute less than 10% to the time required for transcript synthesis. As a consequence the phase of transcription during which TTP is incorporated may not be the rate limiting step in synthesis of the runoff transcript even for the w.t. enzyme. These considerations imply that one need not expect to see marked differences in synthesis of a relatively short runoff transcript by Y639F or the w.t. enzyme when TTP is substituted for UTP.

Lanes u and v show reactions in which two rNTPs have been substituted with dNTPs (dATP and dCTP), and lanes w and x show reactions in which three rNTPs have been substituted with dNTPs (dATP, dCTP, and TTP). Synthesis of the 59 base runoff transcript is observed with the mutant polymerase (lanes v and x) indicating that Y639F can carry out synthesis even when 3 rNTPs are substituted with dNTPs.

While the abortive transcript patterns in lanes v and x may largely be described as a combination of the patterns observed in lanes h and 1 there are some important distinctions. The transcript patterns in lanes v and x reveal that the structure of the transcript, as well as the structure of the NTP, affect the rate at which NMPs are added to the transcript. For example, in lanes v and x there is an increase in termination at the 6mer length relative to lane 1 (the 6mer in lanes v or x runs slightly slower than the poly-G 5mer in the adjacent lane). In lanes 1, v and x synthesis of the 7mer involves incorporation of dCMP but in lanes v and x the 6mer contains a dAMP at its 3' end and in lane 1 it contains an rAMP.

The increase in termination at the 6mer point in lanes v or x indicates that the presence of a dNMP on the 3' end of the transcript reduces the ability of the polymerase to further incorporate NMPs. The high level of termination after synthesis of the rGrGrGdA 4mer in lane h relative to the observed termination after synthesis of the rGrGrGrA 4mer in lanes c or d similarly indicates that the presence of deoxynucleotides in the transcript, at least at the 3'-end, influences subsequent extension of the transcript.

Figure 2A:
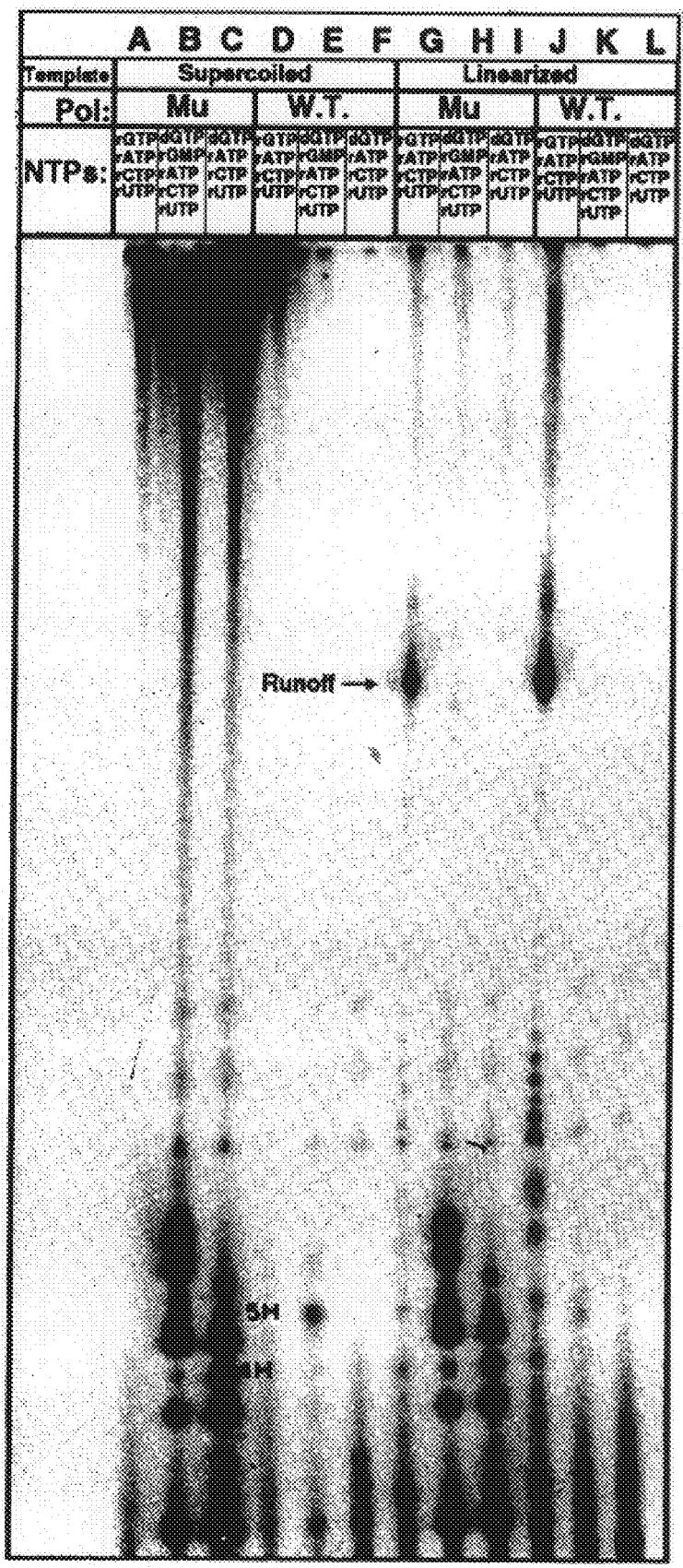
FIG. 2 shows the effect of dGTP substitution on transcription by the w.t. and Y639F polymerase.
Figure 2B:
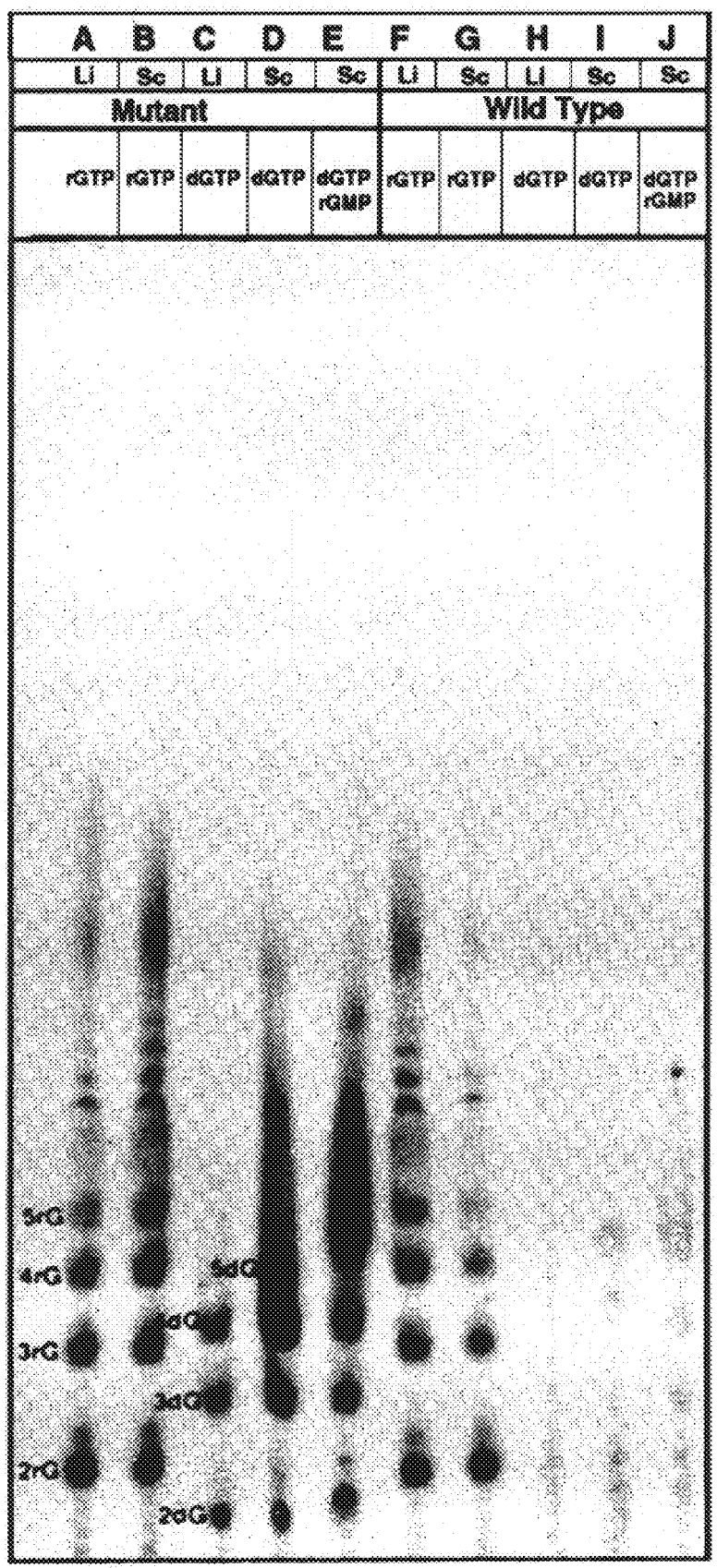

FIG. 2 shows the effect of dGTP substitution on transcription by the w.t. and Y639F polymerase. Polymerases, template (supercoiled(Sc) or HindIII linearized (Li) pT75), and NTPs were as indicated. Polymerase and template concentrations and electrophoresis conditions as in FIG. 1. Left panel: Labeling was with $\alpha$-P$^{32}$ rGTP (a, d, g, j) or $\alpha$-P$^{32}$ dGTP(all other lanes). The runoff transcript from the HindIII-cut template is indicated in lane f. Right panel: Labeling was with $\alpha$-P$^{32}$-rGTP (a, b, f, g) or $\alpha$-P$^{32}$-dGTP (all other lanes). Poly-rG and poly-dG products of various sizes are indicated in lanes a, c, d. Alignment of these transcript patterns with those in lanes b, c, h, and i in the left panel reveals that the added complexity of the transcript pattern in the latter set of lanes is due to the presence of a mixture of heterogeneous sequence and poly-G transcripts. Heterogenous sequence abortive transcripts are indicated in lane c of the left panel ("4H", "5H").

FIG. 2 reveals the effects of substituting dGTP for rGTP in transcription reactions with the w.t. or Y639F polymerase. In reactions containing only dGTP and HindIII-cut pT75 as the template, the mutant polymerase synthesizes poly-dG transcripts up to 4 bases in length (lane c, right panel). Note that—consistent with the assumed structural differences—the poly-dG transcripts ("2dG", "3dG", etc.) in lane c do no co-migrate with the poly-rG transcripts ("2rG", "3rG", etc.) in lane a despite length and sequence identity. When a supercoiled template is used, poly-dG transcripts up to 5 bases in length are obtained (lane d, right panel). In lane e rGMP is added to reactions which contain only dGTP. Ribo-GMP can serve as the initiating, but not elongating nucleotide during transcription( Martin and Coleman, 1989). With rGMP we therefore ask whether either polymerase can elongate with dGTP if an rNMP is provided for initiation. Addition of rGMP to reactions with dGTP further extends the lengths of the transcripts obtained with the mutant polymerase (lane e, right panel). With the w.t. enzyme very little synthesis is observed in reactions with dGTP (lanes h–j, right panel), though the normal pattern of poly-rG synthesis is observed in the rGTP reactions (lanes f, g, right panel).

When reactions contained three rNTPs and dGTP synthesis of runoff transcript from the HindIII-cut template is reduced much more than in reactions in which rGTP is present but other ribonucleotides are substituted with deoxynucleotides. For example, there is very little runoff transcript in lane h of the left panel of FIG. 2. Addition of rGMP increases the amount of runoff transcript made by the mutant enzyme in a reaction containing dGTP (lane i) but the amount of runoff transcript is still much less than in reactions with rGTP. On a supercoiled template (lanes a–c, left panel) high levels of long transcripts are obtained with the mutant enzyme in the reactions with dGTP. The w.t. enzyme shows no transcript synthesis in any of the reactions with dGTP irrespective of whether supercoiled templates or rGMP is used.

Examination of FIG. 2 shows that the marked reduction in runoff transcript synthesis by the mutant enzyme in reactions with dGTP is not due to a deficit in initiation. In fact, in all of the reactions with dGTP we observe abundant synthesis of 2–~6 base transcripts with the mutant enzyme. The low level of runoff transcript synthesis means that these short transcripts are being inefficiently extended to greater lengths. It should also be noted that the abortive transcript pattern seen in lanes b, c, h, and i of the left h panel in FIG. 2 is too complex to be accounted for by presuming one product of each base length. Aligning the transcripts produced in the presence of dGTP only with those produced with dGTP, rUTP, rCTP, and rATP allows us to identify the predominant abortive transcripts in lanes c, d, h, and i of the left panel as poly-dG products. In lane c of the left panel we indicate the major non poly-dG abortives by "4H" and "5H". In lanes b, c, h, and i of the left panel of FIG. 2 we therefore see a pattern similar to that of lane h in FIG. 1. The presence of a mixture of normally extended heterogenous sequence and poly-G abortive transcripts indicates that 'normal' transcript extension is inefficient.

It has been shown that mutations in T7 RNAP that reduce phosphodiester bond formation rates cause poly-rG transcript synthesis even when 4 rNTPs are present (Bonner, et al., 1994). It can be seen that the ratio of poly-G to heterogenous sequence transcripts in lanes b, c, h, i of the left panel of FIG. 2 is greater than in lane h of FIG. 1, indicating a greater deficiency in normal transcript extension when dGTP is substituted for rGTP than when dATP is substituted for dGTP. Note that this occurs even though normal extension of the dGdGdG trimer in lane i of the left panel of FIG. 2 (for example) would involve addition of a ribo-AMP while extension of the rGrGrG trimer in lane h of FIG. 1 would involve addition of a deoxy-AMP, clearly highlighting the role of transcript structure, as well as substrate structure, in determining the efficiency of transcript extension. These results show that Y639F can initiate and elongate transcripts with dGTP substituted for rGTP but normal extension of the transcripts in the 2–8 base range is impaired leading to a large increase in the proportion of poly-dG and short transcripts synthesized. Addition of rGMP to serve as the initiating nucleotide and the use of a supercoiled template both enhance the ability of the mutant to extend the short transcripts during the initial stages of transcription.

Barriers to initiation and extension of the initial transcript with dNTPs: FIG. 2 reveals that Y639F can efficiently transcribe with dGTP the initial G segment of a promoter that initiates "GGGA" but is severely blocked in extending the dG trimer with the A. This implies that the sequence of the initially transcribed region may influence the efficiency with which Y639F can extend the transcript when using dNTPs. FIG. 2 also shows that supercoiling, which presumably facilitates unwinding of the template, enhances the activity of Y639F when using dNTPs. To evaluate the effects of sequence and single-strandedness in the initially transcribed region on the activity of Y639F when using dNTPs, we examined transcription from a set of synthetic promoters which differed in the sequence of their initially transcribed regions and in being fully double-stranded or single-stranded in their initially transcribed regions (FIG. 3).

Figure 3:
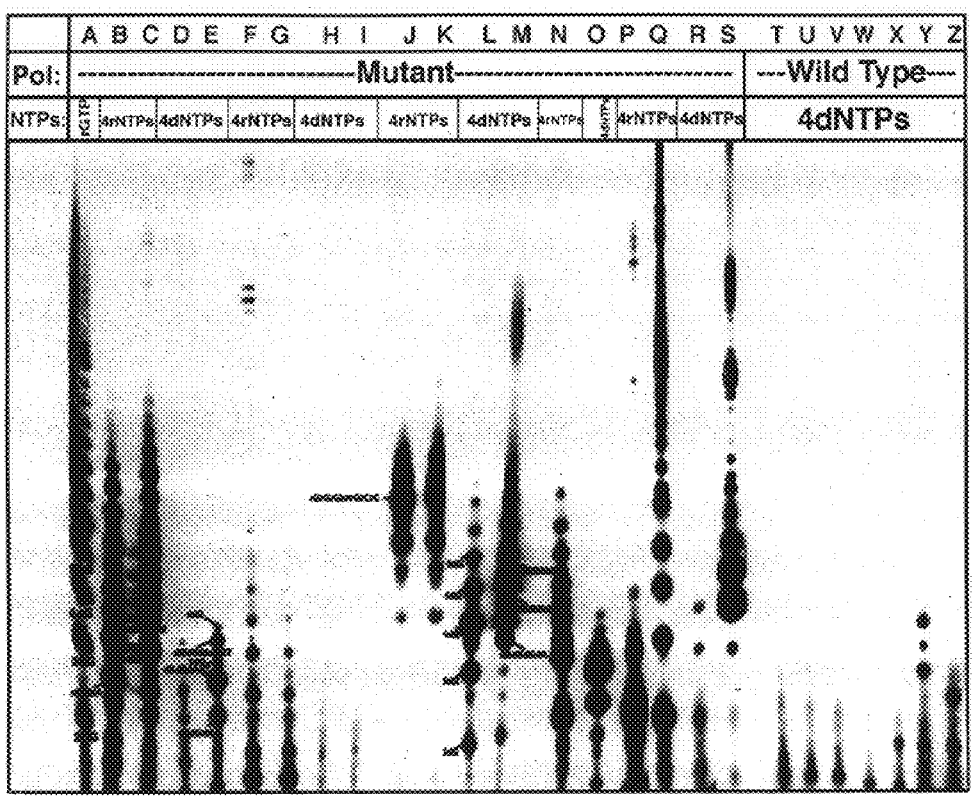
FIG. 3 shows the effects of single-strandedness and sequence in the initially transcribed region on the activity of Y639F in reactions with 4 rNTPs or 4 dNTPs.

FIG. 3 shows the effects of single-strandedness and sequence in the initially transcribed region on the activity of Y639F in reactions with 4 rNTPs or 4 dNTPs. Poly-rG transcripts of various sizes are indicated in lane a. Reactions contained the indicated NTPs and polymerases. Polymerase and promoter concentrations were $10^{-6}$ M and $10^{-5}$ M, respectively. NTP concentrations and electrophoresis as in FIG. 1. Indicated in some of the lanes are the sequences of different transcripts as deduced from alignment with poly-rG or poly-dG ladders synthesized in the presence of rGTP or dGTP only. The synthetic promoter templates used are double-stranded and have the sequence— CGAAATTAATACGACTCACTATA (SEQ ID NO:2)—in their −23 to −1 regions. The promoters differ in their initially transcribed regions as follows: b–e, t, u: GGACT; f–j, v, w: GAGACCGG; a, j–m, x, y: GGGAGACC; n, o, z: GGAAAATT; p–s: GGGGGGGGGGGACT (SEQ ID NO:3). The promoters also differ in being double-stranded (b, d, f, h, j, l, p, r) or single-stranded (other lanes) in their transcribed regions.

For most of the promoters tested, transcription with rNTPs was not markedly affected by having the initially transcribed region be single-stranded. However, when transcribing with 4 dNTPs, Y639F was more active on the partially single-stranded promoters. For example, in lane e (partially single-stranded promoter) of FIG. 3 transcription products are both more abundant and extend to greater lengths than in lane d, where the promoter is fully double-stranded. A similar comparison may be made between lanes m and l or s and r. Regarding sequence we found that a promoter which initiated with 3 G's was superior to a promoter which initiated with two, which was in turn superior to a promoter which initiated with just one G. Thus Y639F activity when using dNTPs was greatest on a promoter which initiates "GGGAGACC" (lanes l and m). The initially transcribed region of this promoter corresponds to the consensus sequence for T7 promoters in the +1 to +6 segment. This was the only promoter which, when fully double stranded, gave rise to high levels of transcript synthesis with Y639F in reactions containing only dNTPs (lane 1).

Promoters which initiated with 2 G's (lanes d, e, o) gave lower levels of transcript synthesis in the 4 dNTP reactions, and a promoter which initiated with 1 G (lanes h, i) was not utilized by Y639F in reactions with 4 dNTPs. Within the initially transcribed region, elements other than the number of G's appear to be important. For example, we have found that the w.t. or Y639F polymerases are less efficient in initial transcription extension on the T7 promoter found in the pBS plasmid which initiates GGGC, than on the φ10 promoter found in pT75 which initiates with the consensus GGGAGA (data not shown).

Another example is evident in lanes n and o which show the transcripts obtained on a partially single-stranded promoter that initiates GGAAAAUU. Like the promoter used in lanes c and e, this promoter initiates with 2 G's but normal transcript extension on this promoter is less efficient than on the promoter that initiates GGACU. In the 4 rNTP reactions (lanes c, n), the proportion of short transcripts (dimers, trimers) is greater in lane n and we observe significant amounts of poly-rG transcripts beyond the dimer length in lane n but not in lane c. In the 4 dNTP reactions almost all of the transcripts in lane o terminate at the trimer or tetramer length. Because increasing the number of Gs from 1 to 3 enhanced Y639F activity when using dNTPs, we tested a promoter which initiated with a run of 11 G's (lanes p–s). A potential drawback to such a promoter is that such a long run of G's could inhibit the ability of the polymerase to unwind the template. Since T7 promoters with more than 3 consecutive G's in the initial region do not occur naturally, it may be that for other reasons such sequences do not favor initial transcript extension. In fact, we find that this promoter is a poor template. When it is fully double-stranded, initiation and extension of the transcript is inefficient with either rNTPs (lane p) or dNTPs (lane r), consistent with the expectation that a promoter with this sequence would be difficult to melt. Initiation and transcript extension is enhanced when this promoter is partially single-stranded (lanes q and s), but while poly-G transcripts from 2 to 7 or more bases in length are abundant, runoff transcripts of the expected length are not predominant products. In reactions with 4 rNTPs the transcript patterns of the w.t. and Y639F polymerases are virtually identical so we do not repeat the 4 rNTP reactions with the w.t. enzyme in FIG. 3. Lanes t–z show that the w.t. enzyme is virtually inactive in reactions with 4 dNTPs and the same set of promoter used in lanes b–s.

Relative selectivity of the mutant and w.t. polymerases for dNTPs and rNTPs: FIGS. 1–3 present a qualitative analysis of the structure of the transcripts produced by the w.t. and Y639F polymerases with various combinations of NTPs. They show that Y639F can use dNTPs with high efficiency and that both transcript and substrate structure play a role in determining the efficiency of transcript extension. To obtain a quantitative measure of the relative selectivity of the w.t. and mutant polymerases for dNTPs vs. rNTPs under conditions where transcript structure was not a complicating factor, we carried out reactions in which all 4 rNTPs were present but rNTPs or dNTPs were used to radiolabel the transcripts (Table I, see Appendix 1). Under these conditions the unlabeled rNTPs were present in vast excess relative to the labeling NTPs so labeling dNTPs are almost always incorporated adjacent to rNTPs and into transcripts of nearly uniform rNMP structure. On average the mutant enzyme is ~20-fold less selective for rNTPs over dNTPs than the w.t. enzyme. We used this assay to screen our collection of T7 RNAP active site mutants for increased dNTP utilization. In this screen we looked for increased dATP incorporation in transcription reactions with all of these mutants using supercoiled pT75 as the template, 4 cold rNTPs, and $P^{32}$-rATP or $P^{32}$-dATP to label. Since these results were negative with the exception of the tyrosine 639 mutants, we do not present them here, but the mutants tested in this way are listed in "Materials and Methods". It has been reported that use of $Mn^{++}$ instead of $Mg^{++}$ decreases substrate discrimination and increases miscoding for a number of polymerases (Tabor and Richardson, 1989; Nivogi and Feldman, 1981). We, therefore, examined the rNTP/dNTP selectivity of the mutant and w.t. enzymes in $Mn^{++}$-citrate buffer (Tabor and Richardson, 1989). With $Mn^{++}$ the preference of both the w.t. and Y639F polymerases for rNTPs over dNTPs was markedly reduced.

Relative activity of the w.t. and Y639F polymerases with different NTP combinations: The relative activities of the Y639F and w.t. polymerases with supercoiled pT75 as a template and various combinations of rNTPs/dNTPs were measured in both $Mg^{++}$ and $Mn^{++}$ buffers (Table II, see Appendix 1). In $Mg^{++}$ buffer, substitution of a single rNTP with a dNTP reduces w.t. activity by 20 to >400-fold, but only modestly reduces the activity of Y639F. The rank order of the effect of a particular dNTP substitution on w.t. enzyme activity—dGTP>dATP>dCTP>dTTP=dUTP—matches the order of their addition to the transcript. With the "2 dNTP" reactions the w.t. enzyme was most active when rCTP and rUTP were substituted with dNTPs, corresponding to the 2 nucleotides added latest to the transcript. The w.t. enzyme was inactive with all other "2 dNTP" or "3 dNTP". In the "2 dNTP" reactions Y639F was least active in the dGTP, dATP reaction, corresponding to the 2 nucleotides incorporated first during transcription. In the "3 dNTP" reactions Y639F was least active in the dGTP, dATP, dCTP reaction, corresponding to the 3 nucleotides incorporated first during transcription.

In $Mn^{++}$ buffer both the w.t. enzyme and Y639F show a reduction in their sensitivity to substitution of dNTPs for rNTPs, consistent with an expectation of reduced substrate discrimination in $Mn^{++}$ buffer. There was, however, also a sharp reduction in overall activity with $Mn^{++}$. We varied $Mn^{++}$ concentrations over a wide range (from 20 mM to 150 μM in 2-fold dilutions) to determine if an optimal $Mn^{++}$ concentration that would result in high activity could be identified, but we found similar activity at all $Mn^{++}$ concentrations tested (data not shown). Thus, while discrimination between rNTPs and dNTPs was less in $Mn^{++}$ buffer, Y639F is more active in $Mg^{++}$ buffer than in $Mn^{++}$ buffer with all NTP combinations examined. Similarly, the w.t. enzyme exhibits greatly reduced discrimination between rNTPs and dNTPs in $Mn^{++}$ buffer, but is modestly more active in $Mn^{++}$ buffer than in $Mg^{++}$ buffer only for certain combinations of dNTPs and rNTPs.

DNA and RNA synthesis on homopolymeric templates: T7 RNAP will synthesize poly(rG) RNAs on poly(dC) templates (Bonner, et al., 1994; Ikeda and Richardson 1987). We measured the activity of the w.t. and mutant polymerases on poly(dI).poly(dC) with rGTP, dGTP, dGTP+rGMP (Table III, see Appendix 1). The activity of T7 RNAP on poly(dI)-poly(dC) and poly(dC) is especially robust. Mutant polymerases that have greatly reduced activity on normal promoter templates still display high activity on poly(dC) templates (Bonner, et al., 1994). We, therefore, characterized two poorly active non-conservative tyrosine mutations on this template (Y639A and Y639S). In Table III we also present results obtained with mutant G640A. Presentation of data for the latter mutant was selected because it is more comparable in activity to the Y639A/S mutants and because it is representative of a mutation which has marked effects on the kinetics of transcription but does not affect substrate discrimination, even though it is directly adjacent to Y639. We find that all of the Y639 mutants exhibit reduced substrate discrimination as demonstrated by the fact that their differential activity in reactions containing dGTP or dGTP+rGMP vs. rGTP is less than for the w.t. enzyme or the G640A mutant. In fact Y639F displays similar activity with rGTP, dGTP, or dGTP+rGMP.

Figure 4:
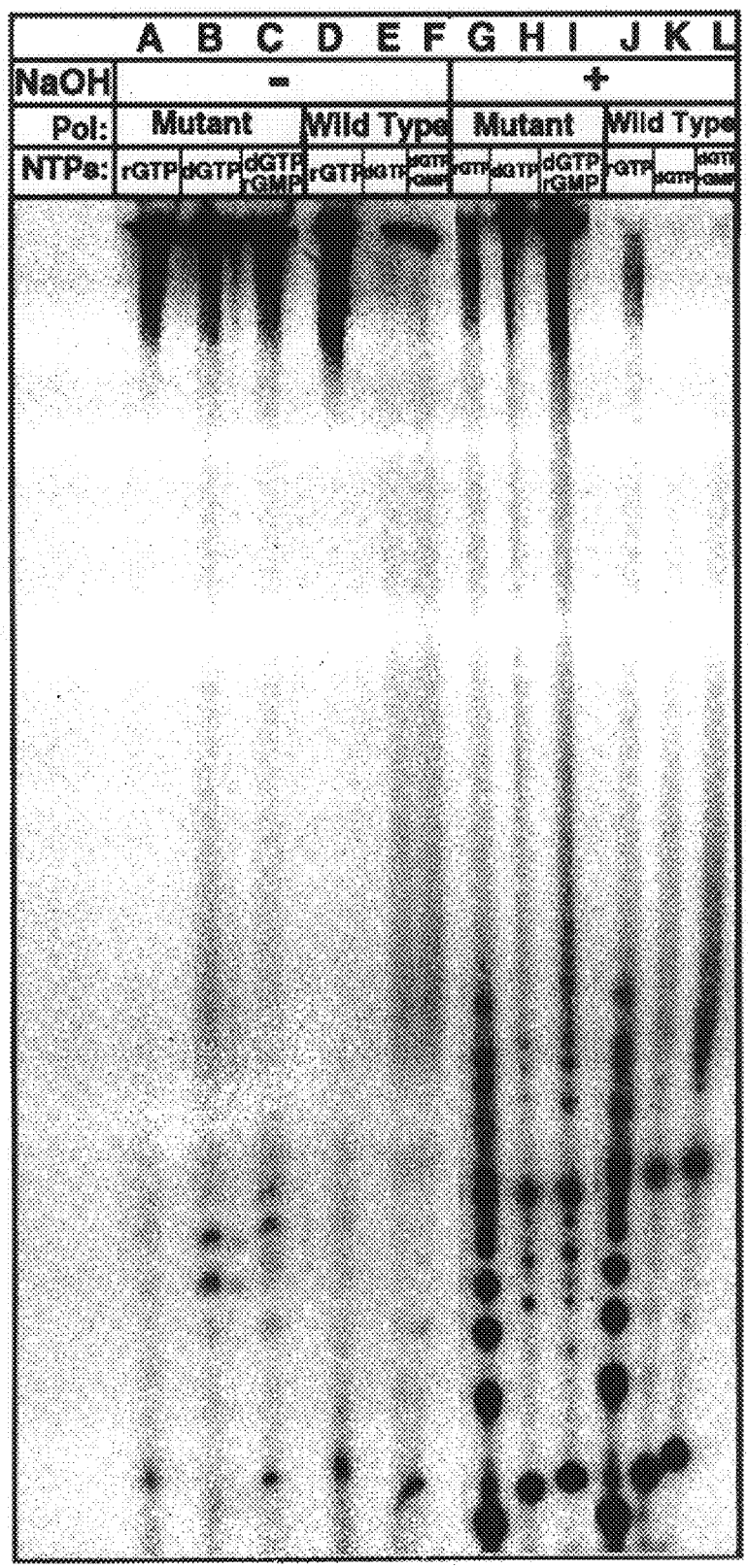
FIG. 4 shows transcription by Y639F and w.t. polymerase with dGTP or rGTP on poly(dI).poly (dC).

Since the nucleic acid synthesized by Y639F on poly(dI) .poly(dC) using dGTP is presumably composed solely of dNMPs it is expected to be resistant to alkaline hydrolysis (Schmidt and Tannhauser, 1945). FIG. 4 shows transcription by Y639F and w.t. polymerase with dGTP or rGTP on poly(dI).poly dC). Transcription reactions were carried out with poly(dI).poly(dC) at 0.2 mg/ml and the indicated NTPs and polymerases. Reaction products were left untreated (−) or treated with 1 M NaOH for 5 hours at 37° C. (+). Polymerase and NTP concentrations and electrophoresis as in FIG. 1. Labeling was with α-$P^{32}$ rGTP (a, d, g, j) or α-$P^{32}$ dGTP (other lanes). FIG. 4 shows the transcription products obtained with the w.t. or Y639F polymerases on poly(dI) .poly(dC) before and after treatment with alkali. With dGTP or dGTP+rGMP the w.t. enzyme is poorly active in the synthesis of long transcripts, however we can observe smears of heterogeneously sized, short transcripts in the reactions with the w.t. enzyme and the dGTP substrates (lanes e and f) while Y639F synthesizes higher levels of long transcripts which are retained near the top of these gels (lanes b and c). The presence of these short transcripts indicates that Y639F and the w.t. enzyme differ only in the degree to which they can utilize dNTPs. The w.t. can also initiate and extend transcripts with dGTP, but it is much less processive when using dNTPs than Y639F so its transcripts are much shorter. When these reactions are treated with base, degradation of the long transcripts made in the reactions with rGTP is observed and the amounts of short RNAs (presumably hydrolysis products) increase (lanes g and j). In the reactions in which dGTP or dGTP+rGMP were used as substrates no degradation of the transcripts by base treatment is observed, confirming that these transcripts are composed of dNMPs.

T7 RNAP as a reverse transcriptase or RNA replicase which initiates de novo: It has been reported that T7 RNAP can use both RNA and DNA templates (Konarska and Sharp, 1989). We, therefore, determined if the Y639F mutant would use dNTPs when transcribing an RNA template (poly(rC), Table IV). Overall the activity of the w.t. and Y639F polymerases on poly(rC) with rGTP was 10–20-fold less than on poly(dC) (not shown), but this reduction did not preclude synthesis of high levels of RNA on poly(rC) by using higher polymerase concentrations than were used in the poly(dI).poly(dC) reactions. When dGTP or dGTP+ rGMP was used the w.t. enzyme was not measurably active on poly(rC), while the activity of Y639F was reduced by only ~4-fold (with dGTP+rGMP) or ~8-fold (with dGTP). Thus, both the w.t. and Y639F polymerases are capable of unprimed RNA-directed RNA polymerization while Y639F is also capable of unprimed reverse transcription.

DNA- and RNA-primed synthesis of DNA and RNA: In the assays described so far we have examined de novo initiated synthesis. T7 RNAP can also extend RNA primers. We, therefore, examined the abilities of both polymerase to carry out DNA or RNA primed synthesis of DNA and RNA (FIG. 5).

Figure 5:
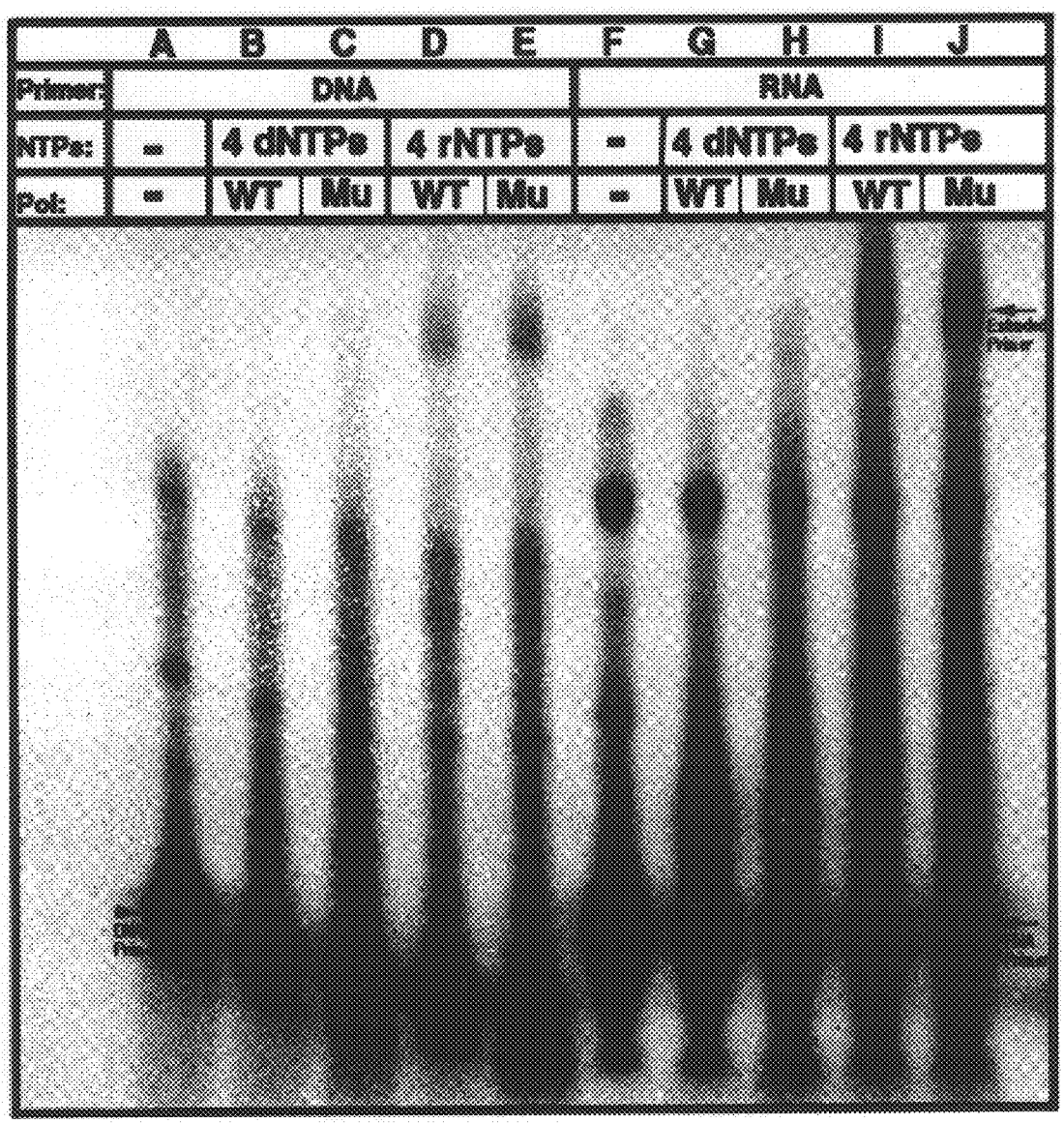
FIG. 5 shows primed synthesis of DNA and RNA with Y639F and the w.t. polymerase.

FIG. 5 shows primed synthesis of DNA and RNA with Y639F and the w.t. polymerase. Transcription reactions contained end-labeled 12 base DNA or RNA primers of identical sequence (GGACACGGCGAA, SEQ ID NO: 4) hybridized to a DNA template (CCCGGGATGGAATG GAGTATTCGCCGTGTCCATGGCTGTAAGTATCC, SEQ ID NO: 5). Primer-template concentration was $10^{-5}$ M. Reactions contained the indicated polymerases ($10^{-7}$ M) and NTPs. NTP concentrations and electrophoresis as in FIG. 1.

We found that both the w.t. and Y639F polymerases can extend DNA and RNA primers with rNTPs, but extension of DNA primers was 2–3-fold less efficient than extension of RNA primers. Y639F also extended DNA and RNA primers with dNTPs but ~4-fold less efficiently than with rNTPs.

The Y639F mutant does not exhibit greatly increased miscoding: We examined the miscoding properties of the w.t. and mutant T7 RNAPs by measuring the relative incorporation of labeled rGTP, rUTP, rATP, and rCTP on poly (dC) or poly(dT) templates in the presence of excess unlabeled rGTP or rATP, respectively (Table V, see Appendix 1). An increase in miscoding would be reflected in an increase in the rate of incorporation of the non-complementary NTP into RNA.

On poly(dC), the w.t., Y639F, and G640A polymerases incorporate rGTP into RNA at greater than 1300–2000-fold the rate of rUTP incorporation. Ribo-GTP is incorporated some 400–600- fold better than rCTP, and 200–400-fold better than rATP. Because of their lower activity we can say only that the relative rate of incorporation of rGTP on poly(dC) is 184-fold greater than the rate of incorporation of non-complementary rNTPs for Y639A, and 50-fold greater for Y639S. The use of $Mn^{++}$ instead of $Mg^{++}$ has been reported to increase miscoding for a number of polymerases (Tabor and Richardson, 1989; Nivogi and Feldman, 1981) so we examined the effects of $Mn^{++}$ on miscoding by w.t. and Y639F polymerases. In $Mn^{++}$ buffer the G640A, Y639A, and Y639S mutants were insufficiently active to allow accurate measures of miscoding. With the w.t. and Y639F polymerases the use of $Mn^{++}$ increases miscoding by 20–40-fold. However, the apparent rate of miscoding by Y639F remains similar to the w.t enzyme.

On poly(dT), high levels of activity allowing an accurate measure of miscoding frequencies could only be observed for Y639F and the w.t. polymerase in both $Mg^{++}$ and $Mn^{++}$ buffers. In $Mg^{++}$ buffer apparent miscoding rates on poly (dT) were higher than on poly(dC), but were similar for Y639F and the w.t. enzyme. In $Mn^{++}$ buffer miscoding rates were increased by ~5-fold, on average, but again rates were similar for w.t. and Y639F. However, on poly(dT) Y639F did show a reproducible ~2-fold increase, relative to the w.t. enzyme, in the ratio of the rates of rGTP to rATP incorporation.

Homopolymer assays have been used previously to measure miscoding by RNAPs (Nivogi and Feldman, 1981; Glazer, 1978; Blank, et al., 1986) but it should be remarked that they can produce only upper bounds for miscoding frequencies Measured miscoding rates could reflect contamination of the homopolymeric templates. It is also possible that the transcripts themselves could serve as templates and support incorporation of rNMPs non-complementary to the original template (i.e., the poly(rG) or poly(rA) transcripts made on poly(dC) or poly(dT) could subsequently support synthesis of poly(rC) or poly(rU) transcripts). Such caveats are less relevant to the miscoding observed in $Mn^{++}$ buffer since the change in divalent cation increases miscoding but cannot affect template composition. However, in $Mg^{++}$ buffer we should consider the measured miscoding frequencies to be upper bounds for the true rates of miscoding. Nevertheless, the results presented in table V indicate that Y639F does not exhibit a gross increase in miscoding which would manifest itself as a clear increase in the incorporation of non-complementary rNMPs on homopolymeric templates.

The increased utilization of dNTPs by Y639F is due to both a decreased $K_m$ and an increased $k_{cat}$ for dNTPs: The $K_m$ and $k_{cat}$ of the w.t. and Y639F polymerases with rATP, rITP and 5 different dNTPs were measured (Table VI, see Appendix 1). The $K_m$ of the w.t. enzyme for dNTPs was much higher than previously reported values for the corresponding rNTPs and varied considerably for different dNTPs (Ikeda and Richardson, 1987; Patra, et al., 1992). Notably the w.t. enzyme $K_m$ values correlate with the rNTP/dNTP selectivity values presented in Table I. The selectivity of the w.t. enzyme with ribo- vs. deoxy-nucleotides was greatest for CTP, followed by ATP, and was the least for UTP, implying that an important component of the selectivity of the w.t. enzyme for rNTPs over dNTPs is a much higher $K_m$ for dNTPs. For Y639F, the $K_m$ values for these dNTPs are from ~3 to ~11-fold less, but the rank order of these $K_m$ values (dCTP $K_m$>dATP $K_m$>dGTP $K_m$>dTTP $K_m$) is the same as for the w.t. enzyme. For Y639F, $k_{cat}$ values for reactions with different dNTPs were only 2–4 fold less than for rNTPs, while the w.t. enzyme displayed $k_{cat}$ values with dNTPs that were from ~6 to ~30-fold less than for rNTPs.

Elongation rates of Y639F in reactions containing a single dNTP: Elongation rates for Y639F in reactions with 4 rNTPs or 1 dNTP and 3 rNTPs were determined by analyzing aliquots, taken at 10 second intervals, from transcription reactions initiated on supercoiled PT75 by adding NTPs to otherwise complete reaction mixes (FIG. 6).

Figure 6:
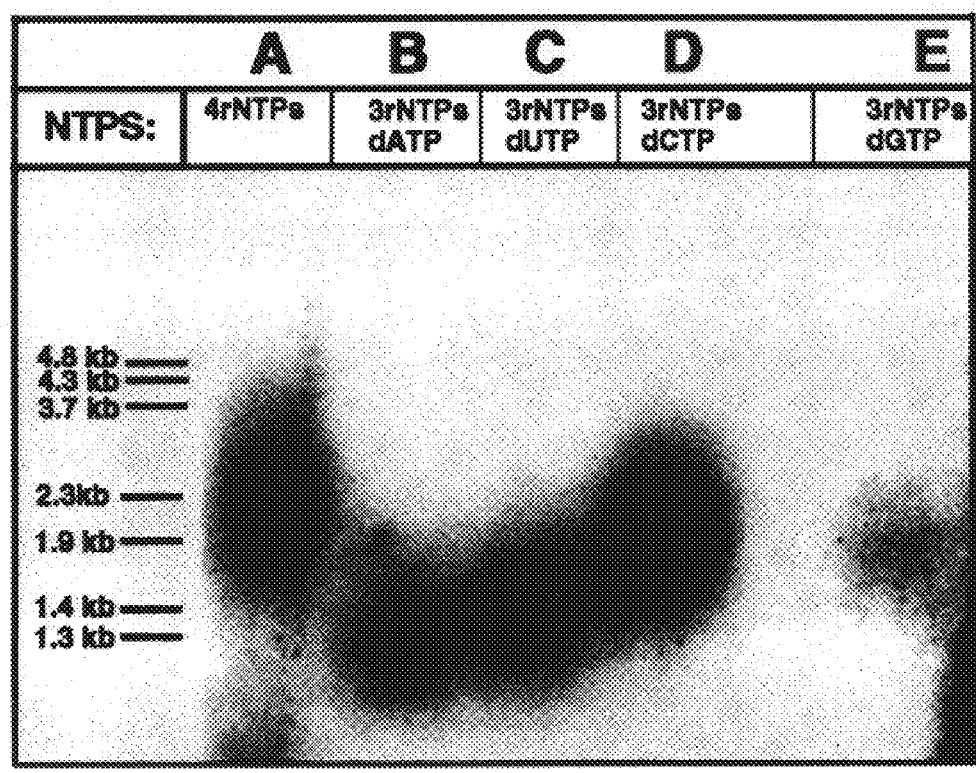
FIG. 6 shows relative elongation rates of Y639F in "4 rNTP" and "3 rNTP+1 dNTP" reactions.

FIG. 6 shows relative elongation rates of Y639F in "4 rNTP" and "3 rNTP+0.1 dNTP" reactions. The template was supercoiled pT75 at $5 \times 10^{-7}$ M. Y639F polymerase was used at a concentration of $10^{-6}$ M. Reactions contained the indicated NTPs. Labeling was with $\alpha$-$P^{32}$-rATP (lane e) or $\alpha$-$P^{32}$-rGTP (other lanes). After initiation of the reactions aliquots were taken at 10 second intervals and analyzed on 1% agarose denaturing-formaldehyde gels. The figure shows the 20 second time point. The bars indicate the positions of $\lambda$ DNA markers.

When analyzed on denaturing agarose gels (FIG. 6) the heterogeneously sized transcripts from these reactions are resolved as a smear with the trailing edge of the smear corresponding to transcripts initiated at t=0 and from which the maximal transcript elongation rate can be determined (Golomb and Chamberlin, 1974; Bonner, et al., 1994). The following elongation rate reductions (relative to a '4 rNTP' reaction) were obtained for reactions containing a 3 rNTPS and 1 dNTP:dATP, ~3-fold; dUTP, ~2-fold; dGTP ~1.5-fold; dCTP, 1–1.5-fold. Because of its poor activity in reactions with dNTPs we could not determine the corresponding elongation rate reductions for the w.t. enzyme.

Other non-canonical nucleoside triphosphate substrates for mutant polymerases: Although wild-type T7 RNAP can not efficiently utilize dideoxy-NTPs as substrates, we have found that Y639 mutants of this enzyme can also use dideoxy-NTPs as substrates (Table VII). We have also found that Y639 mutants can use other non-canonical nucleoside triphosphates as substrates (Table VIII). Nucleic acids synthesized by incorporation of some non-canonical nucleotides, such as 2'-F-NTPs, may offer advantages in being more resistant to digestion by nucleases such as ribonucleases. Other uses and advantages of various non-canonical nucleotide substrates in methods of the present invention using the mutant polymerases will be apparent after examination of the specification, claims and drawings.

Other mutations: It is conceivable that, in the absence of a bound rNTP, a hydrogen bond forms between Y639 and some other active site side chain. The possibility of an interaction between M635 and Y639 was tested since M635 and Y639 are close and M635 approaches the ribose in our models of NTP in T7 RNAP (Huang, et al., submitted for publication). This position is methionine in the T7 RNAP class of RNAPs (McAllister, W. T., 1993), but is either tyrosine or phenylalanine in the homologous DNAPs, and in the DNAP mutants at this site (i.e., positions homologous to position 762 in *E. coli* DNAP I) that affect dNTP/ddNTP discrimination (Tabor. S., and Richardson, C. C., European patent application, 1994). While M635A, M635F or M635Y mutants had effects on NTP $K_m$, they did not affect 2'-group discrimination with respect to dNTPs and rNTPs in either wild-type or the Y639F T7 RNAP background. Additional studies will reveal whether these M635 mutations have other effects, such as effects on discrimination at the 3'-position of the sugar, or effects on discrimination with respect to NTPs with other substituents, such as fluorine at the 2' position of the sugar. Also, studies on similar double mutations at the homologous sites in the homologous class I DNAPs will reveal the effects of such double mutations on discrimination at the 2'- and 3'-positions of the sugar; specifically, these studies will reveal whether class I DNAPs having a phenylalanine at the position homologous to amino acid position 766 in *E. coli* DNAP I have reduced discrimination for rNTPs if the amino acid is methionine or tyrosine at the position homologous to amino acid position 762 in *E. coli* DNAP I.

Provided that class I DNAP mutants which have a reduced discrimination for rNTPs compared to dNTPs can be obtained, it will be possible to use such DNAP mutants to carry out the methods of the present invention that comprise nucleic acid synthesis from a nucleic acid primer, at least part of which is sufficiently complementary to a template nucleic acid to hybridize therewith and to be extended by the polymerase. An especially preferable use for such mutant DNA polymerases would be to carry out Partial Ribo-substitution sequencing reactions from primers, whether labelled by any of the methods known in the art, or unlabelled. Since the sequence-delimiting rNTP nucleotides for the Partial Ribo-substitution Reaction do not terminate the growing phosphodiester chain when they are incorporated during nucleic acid synthesis, the DNA synthesis for Partial Ribo-substitution can occur simultaneous with and be identical to nucleic acid synthesis for another procedure, such as NASBA, 3SR, TMA or another similar method, provided that the mutant DNAP with reduced discrimination for rNTP compared to dNTPs is thermostable, or the PCR strand displacement amplification or other methods for nucleic acid amplification involving nucleic acid synthesis from a primer. The nucleic acid products containing the sequence-delimiting rNMPs can then be cleaved by treatment with a chemical base or a ribonuclease, and analyzed by methods known in the art to obtain the nucleotide-specific pattern of bands or, provided that a Partial Ribo-substitution Reaction is carried out for each of the four nucleotides, the complete sequence of the nucleic acid. Also, provided that primers with distinguishable non-radioactive labels are used, multiple Partial Ribo-substitution sequencing reactions may be carried out simultaneously in the same reaction mixture and run and read in the same lane of a polyacrylamide gel or capillary tube or other matrix for separating the fragments based on size, as is the case for all of the methods of the present invention described herein.

C. Discussion

Our results reveal that mutations of tyrosine 639 in T7 RNAP reduce the ability of the polymerase to discriminate between rNTPs and dNTPs. A conservative mutation which removes the tyrosine hydroxyl but retains the phenolic ring (Y639F) exhibits w.t. activity but an average reduction of ~20-fold in the selectivity for dNTPs over rNTPs (Table I). Non-conservative mutations of this tyrosine (Y639A/S) also display decreased rNTP/dNTP discrimination (Table III), but are less active than the w.t. enzyme. Replacement of an rNTP by a dNTP typically reduces Y639F transcript elongation rates by only a factor of two. Tyrosine 639 is conserved in a large number of DNA-directed RNA and DNA polymerases (Delarue, et al., 1990). In DNAP I, mutations of the Y766 to serine and phenylalanine have been characterized (Polesky, et al., 1989; Carrol, et al., 1991). The Y766S mutation was alone amongst a number of active site mutations characterized in decreasing DNAP I fidelity (increasing miscoding). The Y766F mutation displayed w.t. fidelity and activity. Similarly, the T7 RNAP Y639F mutant displays w.t. kinetics (Bonner, et al., 1992, 1994; Woody, et al., 1994), and the only effect we can identify for this mutation in T7 RNAP is the reduced substrate discrimination reported here. Thus, while T7 RNAP Y639F showed decreased dNTP/rNTP selectivity, it did not exhibit increased miscoding as assessed by incorporation of non-complementary NTPs on homopolymeric templates.

The Y639 T7 RNAP mutations present us with, in one sense, the functional unification of polymerases to go along with their structural unification. The active site of w.t. T7 RNAP is forgiving with regards to template structure (RNA or DNA) or mode of initiation (primed or de novo). A mutation which relaxes the substrate selectivity of this polymerase further expands the range of activities which it can display in vitro. Depending on the substrates and templates presented to it, the Y639F T7 RNAP can act as an RNA- or DNA-directed RNA or DNA polymerase in primed or de novo initiated reactions. Thus it can display a variety of activities normally associated with distinct polymerases, including some entirely novel activities such as de novo initiated reverse transcription or mixed dNMP/rNMP polymer synthesis.

Example 2: A mutant SP6 RNA Polymerase as a DNA Polymerase

After the observations made above with T7 RNAP, we decided to examine bacteriophage SP6 RNA polymerase to determine whether the DNA synthesis properties observed for the mutant T7 RNAP could, as expected, be extended to other mutant polymerases. Bacteriophage SP6 is a lytic phage which infects the bacterial species *Salmonella tryphimurium* (Butler and Chamberlin, 1982). SP6 phage resembles *E. coli* phage T7 and their genomes are comparable in size, gene organization and pattern of gene expression (Kassavetis, et al., 1982).

The phage encoded RNA polymerases are very similar in size (Butler and Chamberlin, 1982) and amino acid sequence (Katani, et al., 1987).

Figure 7:
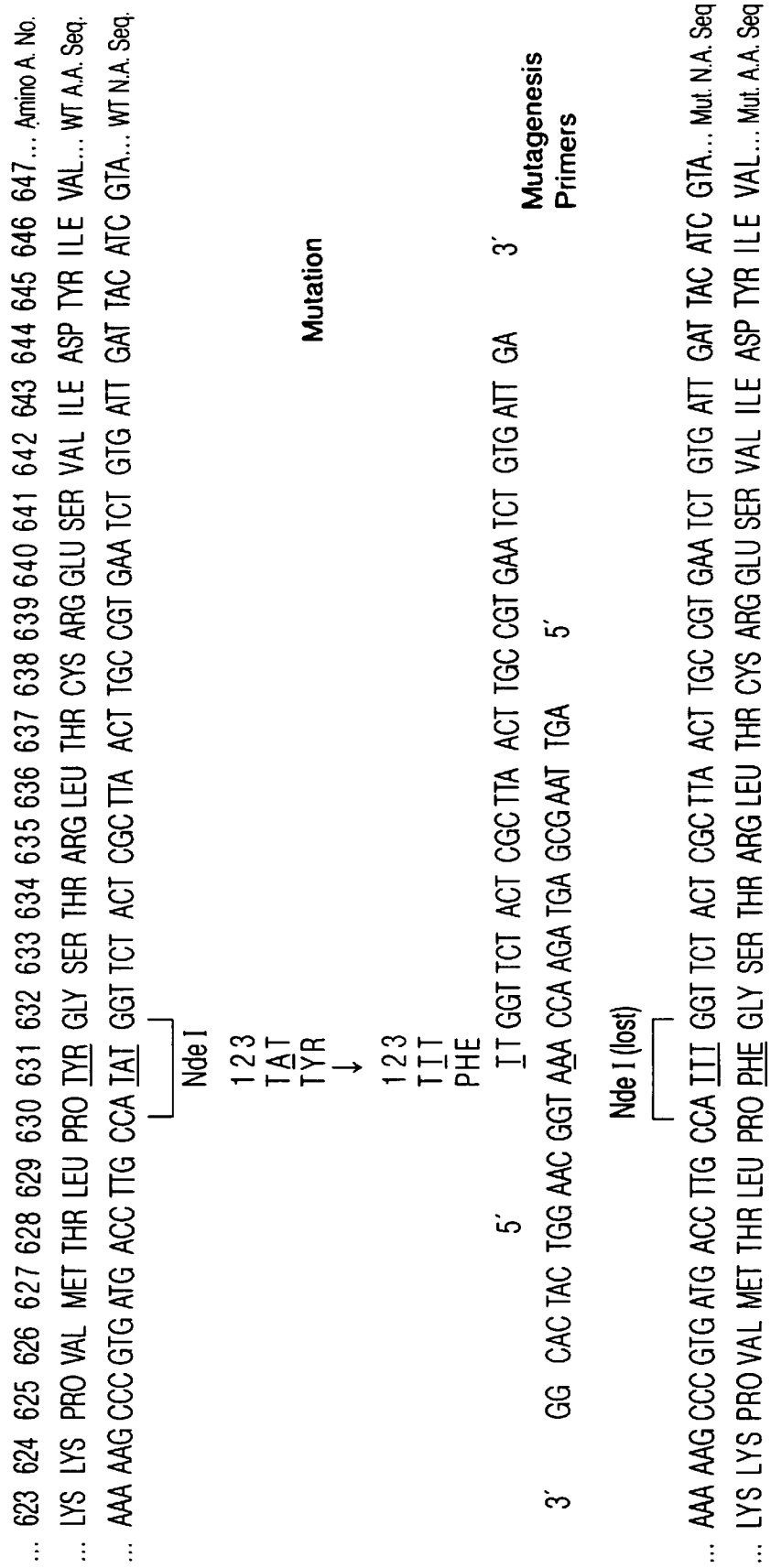
FIG. 7 is a diagram of the mutagenesis strategy involved in creating a mutant SP6 RNA polymerase.

The homologous tyrosine at position 639 in T7 RNA polymerase is readily identified at position 631 in SP6 RNA polymerase (FIG. 7). Substitution of tyrosine 631 with phenylalanine in the SP6 RNA polymerase was expected to confer the same phenotypic changes in catalytic properties in this enzyme as were demonstrated for Y639FT7 RNA polymerase (Example 1).

Localized Mutagenesis. Refer to FIG. 7 for a summary of the amino acid and nucleotide sequence surrounding TYR631 in the SP6 RNA polymerase gene. Mutagenesis of the Y631 residue may be accomplished by the method of Kunkel, et al. (1991). Alternatively, one of the many other methods for mutagenesis known to those of skill in the art may be used. The amino acid and nucleotide sequences of the resulting TYR631PHE mutant SP6 RNA polymerase are also given in FIG. 7. As shown, the A residue at position 2 in codon 631 of the SP6 RNA polymerase gene was changed to a T. This results in the loss of the single NdeI restriction enzyme site which is present in the wild-type gene, permitting identification of mutant clones.

Preparation and Purification of Mutant RNA Polymerase

A single clone was selected in which the NdeI site was missing and which expressed SP6 RNA polymerase activity. Several liters of LB+Amp were grown from a pUC18 Y631F SP6 RNA polymerase clone overnight at 37° C. Cells were harvested, lysed and Y631F mutant SP6 RNA polymerase was purified approximately according to standard methods (Butler and Chamberlin, 1983).

Transcription Reactions

To verify that Y631F SP6 RNAP had the desired phenotype, in vitro transcription reactions were done where one of the four rNTPs was substituted by the corresponding dNTP (Sousa and Padilla, 1995). As expected, the Y631F SP6 RNAP mutant displayed reduced dNTP/rNTP discrimination compared with wild-type SP6 RNAP, similar to that observed for the Y639 mutant of T7 RNAP.

In a standard in vitro transcription reaction using the four ribonucleoside triphosphates (rATP, rGTP, rCTP, and rUTP), both enzymes, the wild-type SP6 RNA polymerase as well as the Y631F mutant, synthesized the correct 1.4 kb transcript and in the expected amounts as visualized on gels. However, if one of the four ribonucleoside triphosphates, rGTP for example, is completely substituted by dGTP and in vitro transcription reactions are done with the wild-type and mutant enzymes, no transcript is made by the wild-type enzymes. However, the mutant enzyme makes the expected full length transcript in good yield as observed on agarose gels.

Appendix 1

TABLE I

Relative Selectivity of Y639F and W.T. Polymerase for rNTPs vs. dNTPs

|  | rATP/dATP | rUTP/dTTP | rCTP/dCTP | rGTP/dGTP |
|---|---|---|---|---|
| Y639F | 8.5–10 (Mg)* | 1.7–1.9 | 2.4–2.5 | .93–1.6 |
|  | .9–1.0 (Mn)* | .48–.76 | .55–.80 | .98–.99 |
| W.T. | 72–83 (Mg)* | 22–25 | 110–150 | 51–67 |
|  | 6–14 (Mn)* | 2.3–2.8 | 4.3–5.1 | 4.4–6.3 |

Reactions were carried out with all 4 rNTPs (0.5 mM) in great excess over radioactive rNTPs or dNTPs. Relative selectivity was determined from the relative percentages of radioactive rNTP vs. dNTP incorporated into RNA. Maximal incorporation was less than 30% of total input radioactivity with all data points used so as to limit effects due to changing NTP concentrations during the experimental time course. The numbers shown give the range for 2 experiments.

*For each rNTP/dNTP and polymerase the upper numbers are those obtained in Mg$^{++}$ buffer, the lower numbers are from Mn$^{++}$ buffer. Polymerases at 10$^{-8}$ M. Template was supercoiled pT75 at 10$^{-7}$ M.

TABLE II

Relative Activity of Y639F and W.T. Polymerase with Different rNTP/dNTP Mixes

|  | W.T. (Mg$^{++}$) | Y639F (Mg$^{++}$) | W.T. (Mn$^{++}$) | Y639F (Mn$^{++}$) |
|---|---|---|---|---|
| 4 rNTPs | 200 | 200 | 21–23 | 9 |
| 3 rNTPs, dTTP | 11–13 | 90–96 | 7–8 | 4 |
| 3 rNTPs, dUTP | 9–11 | 82–91 | 10–11 | 7–8 |
| 3 rNTPs, dATP | 1–2 | 73 | 1–2 | 2–3 |
| 3 rNTPs, dCTP | 4–9 | 86 | 15 | 7–11 |
| 3 rNTPs, dGTP, rGMP | <.5 | 95–109 | 1–3 | 1.4–2.5 |
| 3 rNTPs, dGTP | <.5 | 43–63 | .5–2 | 3 |
| 2 rNTPs, dCTP, dUTP | 2–6 | 27–29 | 3 | 4–7 |
| 2 rNTPs, dCTP, dTTP | 2 | 30 | 5–7 | 5 |
| 2 rNTPs, dCTP, dATP | <.5 | 20–29 | .5–.9 | 4–7 |
| 2 rNTPs, dTTP, dGTP, rGMP | <.5 | 13–15 | <.5 | 3–6 |
| 2 rNTPs, dATP, dTTP | <.5 | 11–14 | <.5 | 3–4 |
| 2 rNTPs, dCTP, dGTP, rGMP | <.5 | 11–14 | <.5 | 2–5 |
| 2 rNTPs, dATP, dGTP, rGMP | <.5 | 5–6 | <.5 | 1–1.5 |
| 1 rNTP, dCTP, dATP, dTTP | <.5 | 12–14 | <.5 | .7–2 |
| 1 rNTP, dCTP, dATP, dUTP | <.5 | 10–11 | <.5 | 2–3 |
| 1 rNTP, dTTP, dCTP, dGTP* | <.5 | 10–13 | <.5 | 2–4 |
| 1 rNTP, dTTP, dATP, dGTP* | <.5 | 11 | <.5 | 1.5–2 |
| 1 rNTP, dCTP, dATP, dGTP* | <.5 | 3–5 | <.5 | 1–2 |
| 4 dNTPs, rGMP | <.5 | <.5 | <.5 | .5 |

*These reactions also contain rGMP. Numbers give ranges from 2 experiments. Template was supercoiled pT75 (10$^{-7}$ M), polymerases at 10$^{-8}$ M (in Mg$^{++}$ buffer) or 10$^{-7}$ M (in Mn$^{++}$ buffer). rNTPs, rGMP, dTTP were at 0.5 mM; dATP, dGTP were at 1 mM; dUTP was at 2.5 mM, dCTP was at 5 mM. From top to bottom the labeling NTPs were: α-P$^{32}$ rGTP, α-P$^{32}$ rCTP, α-P$^{32}$ rCTP, α-P$^{32}$ dATP, α-P$^{32}$ dCTP, α-P$^{32}$ dGTP, α-P$^{32}$ dGTP, α-P$^{32}$ dCTP, α-P$^{32}$ dTTP, α-P$^{32}$ dCTP, α-P$^{32}$ dTTP, α-P$^{32}$ dTTP, α-P$^{32}$ dCTP, α-P$^{32}$ dATP, α-P$^{32}$ dTTP, α-P$^{32}$ dCTP, α-P$^{32}$ dTTP, α-P$^{32}$ dTTP, α-P$^{32}$ rCTP, α-P$^{32}$ dCTP.

TABLE III

Relative activity on poly(dI).poly(dC)

|  | W.T. | Y639F | G640A | Y639A | Y639S |
|---|---|---|---|---|---|
| rGTP | 1000 | 1000 | 240 (200–270) | 145 (142–151) | 48 (47–50) |
| dGTP | 7.4 (5.4–12.5) | 964 (684–1257) | <5 | 5.3 (4.8–5.5) | .6 |
| dGTP + rGMP | 25 (20–27) | 1070 (816–1457) | <5 | 25 (17–30) | 4.4 |

Numbers give mean and range from 3 experiments. Templates were at 0.2 mg/ml, polymerases at 10$^{-8}$ M. Labeling NTPs were α-P$^{32}$ rGTP, α-P$^{32}$ dGTP, α-P$^{32}$ rATP, α-P$^{32}$ dATP, as appropriate. rNTPs or rNMPs at 0.5 mM; dNTPs at 1 mM.

TABLE IV

W.T. and Y639F activity on an RNA (poly(rC)) template

|  | .5 mM GTP | 1 mM dGTP | 1 mM dGTP + .5 mM GMP |
|---|---|---|---|
| w.t. | 1000 | <.5 | <.5 |
| Y639F | 505 (358–733) | 62 (48–80) | 116 (90–148) |

Numbers give mean and range from 3 experiments. Template was at 0.2 mg/ml, polymerases at 10$^{-6}$ M. Labeling NTPs were α-P$^{32}$ rGTP, α-P$^{32}$ dGTP.

TABLE V

Relative rates of incorporation of complementary and non-complementary rNTPs on homopolymeric templates by w.t. and mutant polymerases

|  | W.T. | Y639F | G640A | Y639A | Y639S |
|---|---|---|---|---|---|
|  | I. Template: poly(dC) | | | | |
| GTP/UTP | >2000 (Mg$^{++*}$) | >1760 | >1320 | >184 | >50 |
|  | 53 (Mn$^{++}$)* | 55 | n.d. | n.d. | n.d. |
| GTP/CTP | 400 | 550 | 508 | >184 | >50 |
|  | 32 | 40 | n.d. | n.d. | n.d. |
| GTP/ATP | 233 | 338 | 388 | >184 | >50 |
|  | 9.3 | 8 | n.d. | n.d. | n.d. |

TABLE V-continued

Relative rates of incorporation of complementary and non-complementary rNTPs on homopolymeric templates by w.t. and mutant polymerases

|  | W.T. | Y639F | G640A | Y639A | Y639S |
|---|---|---|---|---|---|
| II. Template: poly(dT) | | | | | |
| ATP/GTP | 170 | 94 | n.d. | n.d. | n.d. |
|  | 50 | 27 | n.d. | n.d. | n.d. |
| ATP/UTP | 121 | 94 | n.d. | n.d. | n.d. |
|  | 21 | 20 | n.d. | n.d. | n.d. |
| ATP/CTP | >340 | >94 | n.d. | n.d. | n.d. |
|  | 77 | 60 | n.d. | n.d. | n.d. |

Numbers are averages from 2 experiments and reflect the ratio of the percentages of labeled rNTPs incorporated into RNA in reactions in which unlabeled complementary rNTPs were in great excess (.5 mM) to labeled complementary or non-complementary rNTPs. Templates were at 0.1 mg/ml. Polymerases were at $10^{-8}$ M in $Mg^{++}$ buffer and $10^{-7}$ M in $Mn^{++}$ buffer.

*The upper number refers to results obtained in $Mg^{++}$ buffer, the lower number to results in $Mn^{++}$ buffer. n.d.: G640A, Y639A, Y639S were poorly active in $Mn^{++}$ buffer, or on poly(dT) under all conditions.

TABLE VI

Kinetic Constants for Y639F and the W.T. polymerase with rNTPs or dNTPs

|  |  | rATP | rITP | dTTP | dUTP | dCTP | dGTP | dATP |
|---|---|---|---|---|---|---|---|---|
| Y639F: | $K_m$ | .063–.125 | .034–.094 | .038–.059 | .052–.092 | .92–1.6 | .185–.264 | .20–.35 |
|  | $k_{cat}$ | 150–210 s$^{-1}$ | 180–200 s$^{-1}$ | 70–110 s$^{-1}$ | 70–130 s$^{-1}$ | 50–90 s$^{-1}$ | 30–60 s$^{-1}$ | 50–70 s$^{-1}$ |
| W.T.: | $K_m$ | .034–.068 | .029–.059 | .209–.262 | 4.4–9.0 | 4.3–13.5 | .602–.701 | 2.0–5.0 |
|  | $k_{cat}$ | 190–220 s$^{-1}$ | 170–230 s$^{-1}$ | 26–29 s$^{-1}$ | 25–39 s$^{-1}$ | 9–14 s$^{-1}$ | 5–9 s$^{-1}$ | 6–9 s$^{-1}$ |

Numbers give ranges from 3 experiments. The template was supercoiled pT75 at $10^{-7}$ M, and polymerases were at $10^{-8}$ M.

TABLE VII

2',3'-dideoxy NTP preferences of the Y639F mutant

| ATP/ddATP | TTP/ddUTP | CTP/ddCTP | GTP/ddGTP |
|---|---|---|---|
| 9.0 | 7.0 | 10.0 | 5.0 |

Numbers reflect the relative specificity ($k_{cat}/K_m$) for an NTP vs. the corresponding ddNTP. Relative specificities could not be evaluated for the wild-type T7 RNAP because the ddNTPs are such poor substrates, but these relative specificities appear to be at least 150-fold.

TABLE VIII

Activity of W.T. and Y639 mutants with NTPs containing different 2'-substituents

| NTP | W.T. | Y639F | Y639M |
|---|---|---|---|
| UTP | 100 | 95 ± 6.7 | 50 ± 1.2 |
| 2'-NH2-UTP | 5.9 ± .27 | 12 ± .41 | 3.6 ± .19 |
| 2'-F-UTP | 3.1 ± .14 | 73 ± 2.6 | 23 ± .72 |
| 2'-dUTP | 2.4 ± .11 | 46 ± 2.4 | 11 ± .46 |
| CTP | 100 | 103 ± 2.3 | 54 ± 3.9 |
| 2'-NH2-CTP | 34 ± .86 | 60 ± 2.5 | 21 ± .38 |
| 2'-F-CTP | 3.4 ± .22 | 63 ± 3.1 | 47 ± .70 |
| 2'-dCTP | 1.6 ± .16 | 57 ± 1.7 | 32 ± 1.1 |
| ATP | 100 | 96 ± 3.0 | 51 ± 1.3 |
| 2'-NH2-ATP | 18 ± .39 | 21 ± .75 | .92 ± .035 |
| 2'-F-ATP | 6.6 ± .12 | 50 ± 1.4 | 9.7 ± .20 |
| 2'-dATP | 2.7 ± .28 | 40 ± 1.3 | 3.2 ± .11 |

Activity was determined with pT75 as template but with one of the rNTPs replaced with a dNTP or a 2'-modified NTP. The labeling NTP was UTP (in reactions with 2'-modified CTPs or ATPs) or CTP (in reactions with 2'-modified UTPs). Y639F and Y639M represent enzymes with substitutions of the wild-type (W.T.) tyrosine at position 639 by phenylalanine (F) or methionine (M), respectively.

Appendix 2

REFERENCES

U.S. PATENTS

U.S. Pat. No. 4,683,202
U.S. Pat. No. 4,965,188

INTERNATIONAL PATENTS

Tabor, S and Richardson, C. C. (Filed 24.11.94) European Patent Application Number 94203433.1; Publication Number 0 655 506 A1.

PUBLICATIONS

Astatke, M., Grindley, N. D. F., and Joyce, C. M. (1995) J. Biol. Chem. 270, 1945–1954.

Axelrod, V. D, Vartikyan, R. M., Aivazashvilli, V. A., and Bebelashvilly, R. S. (1978) Nucleic Acids Res. 5, 3549–3563.

Axelrod, V. D, and Kramer, P.R. (1985) Biochemistry 24, 5716–5723.

Barnes, W. M. (1978) J. Mol. Biol. 119, 83–99.

Beese, L. S., Friedman, J. M., and Steitz, T. A. (1993) Biochemistry 31, 9636.

Blank, A., Gallant, J. A., Burgess, R. R., Loeb, L. A. (1986) Biochemistry 25, 5920–5928.

Bonner, G., Patra, D., Lafer, E. M., and Sousa, R. (1992) EMBO J. 11, 3767–3775.

Bonner, G., Lafer, E. M., and Sousa, R. (1994) J. Biol. Chem. 42, 25120–25128.

Butler, E. T. and Chamberlin, M. J. (1982) J. Biol. Chem. 257, 5772–5778.

Carroll, S. S., Cowart, M., and Benkovic, S. J. (1991) *Biochemistry* 30, 804–13.

Cazenave, C., and Uhlenbeck, O. C. (1994) *Proc. Natl. Acad. Sci. USA* 91, 6972–6976.

Chapman, K. A., and Burgess, R. R. (1987) *Nucl. Acids Res.* 15, 5413–5426.

Chapman, K. A., Gunderson, S. I., Arnello, M., Wells, R. D., and Burgess, R. R. (1988) *Nucl. Acids Res.* 16, 4511–4530.

Compton, J. (1991) *Nature* 350:91–92.

Cotton (1993) *Mutation Res.* 285:125–144.

Cunningham, P. R., and Ofengand, J. (1990) *BioTechniques* 9(6), 713–714.

Duck, P. G., Alvarado-Urbina, B., Burdick, B., and Collier, B. (1990) *BioTechniques* 9, 142–148.

Fahy, et al. (1991) *PCR Methods & Applications* 1, 25–33.

Glazer, R. I. (1978) *Nucleic Acids Res.* 5, 2607–2616.

Golomb and Chamberlin, (1974) *J. Biol. Chem.* 249, 2858–2863.

DeLarue, M., Poch, O., Tordo, N., Moras, D., and Argos, P. (1990) *J. Protein Engineering* 10, 461–467.

Hill, C. S. (1996) "Gen-Probe Transcription-mediated Amplification System Principles," Tech. Bulletin No: L137/01/96, of Gen-Probe, Inc.

Ikeda, R. A., Richardson, C. C. (1987) *J. Biol. Chem.* 262, 2800–3808.

Jacobo-Molina, A, Ding., J., Nanni, R. G., Clark, A. D., Lu, X., Tantillo, C., Williams, R. L., Kramer, G., Ferris, A. L., Clark, P., Hizi, A., Hughes, S. H. & Arnold, E. (1993) *Proc. Natl. Acad. Sci.* (USA) 90, 6320.

Kassavetis, G. A., Butler, E. T., Roulland, D., and Chamberlin, M. J. (1982) *J. Biol. Chem.* 257, 5779–5788.

Katani, H., Ishizaki, Y., Hiraoka, N., and Obayashi, A. (1987) *Nucleic Acids Res.* 15, 2653–2664.

Kohlstaedt, L. A., Wang, J., Friedman, J. M., Rice, P. A., and Steitz, T. A. (1992) *Science* 256, 1783–1790.

Konarska, M. M., and Sharp, P. A. (1989) *Cell* 57, 423–431.

Kramer, F. R., and Mills, D. R., (1978) *Proc. Natl. Acad. Sci. (USA)* 75, 5334–5338.

Kuchta, R. D., Mizrahi, V., Benkovic, P. A., Johnson, K. A., and Benkovic, S. J. (1987) *Biochemistry* 26, 8410–8417.

Kunkel, T. A., Bebenek, K., and McClary, J. (1991) *Methods in Enzymology* 204, 125.

Makarova, O. V., Makarov, E. M., Sousa R., Dreyfus, M. (1995) *Proc. Natl. Acad. Sci. USA.* (submitted).

Martin, C. T., Coleman, J. E. (1987) *Biochemistry* 26, 2690–2696.

Martin, C. T., Muller, D. K., Coleman, J. E. (1988) *Biochemistry* 27, 3966–3974.

Martin, C. T., and Coleman, J. E. (1989) *Biochemistry* 28, 2760–2762.

McAllister, W. T. (1993) *Cellular & Molecular Biol. Res.* 39, 385.

McClure, W. R., and Chow, Y. (1980) *Methods of Enzymology* 64, 277–297.

Milligan, J. F., Groebe, D. R., Witherwell, G. W., and Uhlenbeck, O. C. (1987) *Nucl. Acids. Res.* 15, 8783–8798.

Mizrahi, V., Henrie, R. N., Marlier, J. F., Johnson, K. A., and Benkovic, S. J. (1985) *Biochemistry* 24, 4010–4018.

Moroney, S. E., and Picirrilli, J. A. (1991) *Biochemistry* 30, 10343–10349.

Niyogi, S. K., Feldman, R. P. (1981) *Nucleic Acids Res.* 9, 2615–2627.

Myers and Gelfand, D. (1991) *Biochemistry* 30, 7661–7666.

Patra, D., Sousa, R., and Lafer, E. M. (1992) *J. Mol. Biol.* 224, 307–318.

Pelletier, H., Sawaya, M. R., Kumar, A., Wilson, S. H., and Kraut, J. (1994) *Science* 264, 1891.

Polesky, A. H., Steitz, T. A., Grindley, N. D., and Joyce, C. M. (1989) *J. Biol. Chem.* 265, 14579–14591.

Ricchetti, M. and Buc, H. (1993) *EMBO J.* 12, 387–396.

Sambrook, J., Fritsch, E. F., Maniatis, T., (1989) Cold Spring Harbor Laboratory Press, Cold Spring Harbor, N.Y.

Sanger, et al. (1977) *Proc. Natl. Acad. Sci. (USA)* 74, 5463–5468.

Schmidt, G. and Tannhauser, S. J. (1945) *J. Biol. Chem.* 159, 83–89.

Shi, Y., Gamper, H., Hearst, J. E. (1988) *J. Biol. Chem.* 263, 527–534.

Sawaya, M. R., Pelletier, H., Kumar, A., Wilson, S. H., and Kraut, J. (1994) *Science* 264, 1930.

Sousa, R., and Padilla, R. (1995) *EMBO J.* 14, 4609–4621. (Incorporated by reference as if set forth herein.)

Sousa, R., Lafer, E. M., and Wang, B. -C. (1991) *J. Crystal Growth* 110, 237–246.

Sousa, R., Chung, Y. J., Rose, J. R., and Wang, B. C. (1993) *Nature* 364, 593–599.

Steitz, T. A., Smerdon, S. J., Jager, J., and Joyce, C. M. (1994) *Science* 266, 2022–2025.

Tabor, S., and Richardson, C. C. (1990) *J. Biol. Chem.* 265:8322.

Tantillo, C., Jianoing, D., Jacobo-Molina, A., Nanni, R. G., Boyer, P. L., Hughes, S. H., Pauwels, R., Andiries, K., Janssen, P. A. J., and Arnold, E. (1994) *J. Mol. Biol.* 243, 369–387.

Tabor, S., and Richardson, C. C. (1989) *Proc. Natl. Acad. Sci. USA* 82, 1074–1078.

Tabor, S., and Richardson, C. C. (1985) *Proc. Natl. Acad. Sci. USA* 82, 1074–1078.

Osumi-Davis, P. A., Sreerama N., Volkin, D. B., Middaugh, C. R., Woody, R. W., Woody, A. Y. (1994) *J. Mol. Biol.* 237, 5–19.

We claim:

1. A method for determining sequence of a nucleic acid molecule, comprising the steps of:
   a) synthesizing a nucleic acid molecule de novo from an RNAP promoter sequence in a reaction mixture containing a mutant RNA polymerase in each of four separate reactions, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced discrimination between canonical and non-canonical nucleoside triphosphates, each reaction comprising at least four nucleoside triphosphates, wherein at least one nucleoside triphosphate has a nucleic acid base which is complementary to each of adenine, cytidine, guanine and uracil or thymine and a sugar with either a hydroxy or a hydrogen or a fluorine at the 2'-position, and further comprising a ddNTP, such that each of the four separate reactions forms a plurality of reaction products of differing length, the length of said reaction products indicating the positions or the type of base corresponding to the incorporated ddNTP, and
   b) evaluating the reaction products so that the sequence of the template molecule may be deduced.

2. The method of claim 1, wherein each reaction comprises at least four nucleoside triphosphates chosen from the group consisting of ATP, CTP, GTP, and UTP or rTTP.

3. The method of claim 1, wherein each reaction comprises at least four nucleoside triphosphates chosen from the group consisting of dATP, dCTP, dGTP, dUTP, dTTP, 7-deaza-dGTP, dITP, 5-methyl-dCTP, 5-hydroxy-methyl-dCTP.

4. The method of claim 1, wherein each reaction comprises at least four nucleoside triphosphates chosen from the group consisting of 2'-F-ATP, 2'-F-CTP, 2'-F-GTP, 2'-F-UTP, 2'-F-TTP, 2'-deaza-2'-F-GTP, 2'-F-ITP, and 5-methyl-2'-F-CTP, 5-hydroxymethyl-2'-F-CTP.

5. A method for determining the sequence of a nucleic acid molecule, comprising the steps of:
   a) synthesizing a nucleic acid molecule by extending a primer, wherein at least part of the primer is complementary to a template molecule so as to anneal therewith, in a reaction mixture containing a mutant RNA polymerase in each of four separate reactions, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced discrimination between canonical and non-canonical nucleoside triphosphates, each comprising at least four nucleoside triphosphates, wherein at least one nucleoside triphosphate has a nucleic acid base which is complementary to each of adenine, cytidine, guanine and uracil or thymine and a sugar with either a hydroxy or a hydrogen or a fluorine at the 2'-position, and further comprising a ddNTP, such that each of the four separate reactions forms a plurality of reaction products of differing length, the length of said reaction products indicating the positions of the type of base corresponding to the incorporated ddNTP, and
   b) evaluating the reaction products so that the sequence of the template molecule may be deduced.

6. The method of claim 5, wherein each reaction comprises at least four nucleoside triphosphates chosen from the group consisting of ATP, CTP, GTP, and UTP or rTTP.

7. The method of claim 5, wherein each reaction comprises at least four nucleoside triphosphates chosen from the group consisting of dATP, dGTP, dUTP, dTTP, 7-deaza-dGTP, dITP, 5-methyl-dCTP, 5-hydroxymethyl-dCTP.

8. The method of claim 5, wherein each reaction comprises at least four nucleoside triphosphates chosen from the group consisting of dATP, dCTP, dGTP, dUTP, dTTP, 7-deaza-dGTP, dTTP, 5-methyl-dCTP, 5-hydroxy-methyl-dCTP.

9. The method of claim 1, wherein a dinucleotide or trinucleotide for initiation of de novo acid synthesis is added to the reaction mixture.

10. The method of claim 1, wherein at least one of the nucleoside triphosphates in the reaction mixture is modified to contain a radioactive or non-radioactive label.

11. The method of claim 1, wherein the ddNTP in the reaction mixture is modified to contain a radioactive or non-radioactive label.

12. The method of claim 9, wherein the dinucleotide or trinucleotide in the reaction mixture is modified to contain a radioactive or non-radioactive label.

13. A method for determining the sequence of a nucleic acid molecule, comprising the steps of:
   a) synthesizing a nucleic acid molecule de novo from an RNAP promoter sequence in a reaction mixture containing a mutant RNA polymerase in each of four separate reactions, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced, discrimination between canonical and non-canonical nucleoside triphosphates, each reaction comprising at least four nucleoside triphosphates, wherein at least one nucleoside triphosphate has a nucleic acid base which is complementary to each of adenine, cytidine, guanine and uracil or thymine and a sugar with either a hydrogen or a fluorine at the 3'-position, and further comprising a rNTP, and
   b) treating the nucleic acid products of the reactions so as to bring about hydrolysis of the rNTP has been incorporated, whereby a plurality of reaction products of differing length are formed, the length of said reaction products indicating the positions of the type of base corresponding to the incorporated rNTP,
   c) evaluating the reaction products so that the sequence of the template molecule may be deduced.

14. The method of claim 13, wherein the nucleic acid synthesis is part of or coupled to a method for nucleic acid amplification.

15. A kit for performing the method of claim 13 comprising a mutant nucleic acid polymerase selected from the group consisting of SP6 RNA polymerase comprising an altered amino acid at position 631 and T7 RNA polymerase comprising an altered amino acid at position 639, wherein said mutant RNA polymerase has a reduced discrimination triphosphates and data or instructions describing conditions under which the method of claim 13 may be performed.

16. A kit for performing the method of claim 14 comprising a mutant nucleic acid polymerase which has reduced discrimination between canonical and non-canonical nucleoside triphosphates and data or instructions describing conditions under which the method of claim 14 may be performed.

17. A method for determining the sequence of a nucleic acid molecule, comprising the steps of:
   a) synthesizing a nucleic acid molecule by extending a primer, wherein at least part of the primer is complementary to a template molecule so as to anneal therewith, in a reaction mixture containing a mutant RNA polymerase in each of four separate reactions, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced discrimination between canonical and non-canonical nucleoside triphosphates, each reaction comprising at least four nucleoside triphosphates, wherein at least one nucleoside triphosphate has a nucleic acid base which is complementary to each of adenine, cytidine, guanine and uracil or thymine and a sugar with either a hydrogen or a fluorine at the 2'-position, and further comprising a rNTP,
   b) treating the nucleic acid products of the reactions so as to bring about hydrolysis of the phosphodiester backbone at all sites where a rNTP has been incorporated, whereby a plurality of reaction products of differing length are formed, the length of said reaction products indicating the positions of the type of base corresponding to the incorporated rNTP,
   c) evaluating the reaction products using any of the methods common in the art for separating and detecting products of sequencing reactions so that the sequence of the template molecule may be deduced.

18. The method of claim 17, wherein the nucleic acid synthesis is part of or coupled to a method for nucleic acid amplification.

19. A kit for performing the method of claim 17 comprising a mutant nucleic acid polymerase which has reduced discrimination between canonical and non-canonical nucleoside triphosphates and data or instructions describing conditions under which the method of claim 17 may be performed.

20. A kit for performing the method of claim 18 comprising a mutant nucleic acid polymerase which has reduced discrimination between canonical and non-canonical nucleoside triphosphates and data or instructions describing conditions under which the method of claim 18 may be performed.

21. A kit for performing a partial ribo-substitution reaction comprising a mutant nucleic acid polymerase which has reduced discrimination between canonical and non-canonical nucleoside triphosphates and data or information describing conditions under which the method may be performed.

22. A kit for determining a sequence of a nucleic acid molecule by a dideoxy sequencing procedure, which kit comprises:
   a) a mutant RNA polymerase, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced discrimination between canonical and non-canonical nucleoside triphosphates;
   b) four nucleoside triphosphates; and
   c) four ddNTPs.

23. The kit of claim 22, wherein said nucleoside triphosphates are chosen from the group consisting of ATP, CTP, GTP, and UTP or rTTP and said ddNTPs are ddATP, ddCTP, ddGTP, and ddUTP or ddTTP.

24. The kit of claim 22, wherein said nucleoside triphosphates are chosen from the group consisting of dATP, dCTP, dGTP, dUTP, dTTP, 7-deaza-dGTP, dITP, 5-methyl-dCTP, 5-hydroxy-methyl-dCTP and said ddNTPs are ddATP, ddCTP, ddGTP, and ddUTP or ddTTP.

25. The kit of claim 22, wherein said nucleoside triphosphates are chosen from the group consisting of 2'-F-ATP, 2'-F-CTP, 2'-F-GTP, 2'-F-UTP, 2'-F-TTP, 2'-deaza-2'-F-GTP, 2'-F-ITP, and 5-methyl-2'-F-CTP, 5-hydroxymethyl-2'-F-CTP and said ddNTPs are ddATP, ddCTP, ddGTP, and ddUTP or ddTTP.

26. A kit for determining a sequence of a nucleic acid molecule by a dideoxy sequencing procedure, which kit comprises:
   a) a mutant RNA polymerase, wherein said mutant RNA polymerase is selected from the group consisting of SP6 RNA polymerase comprising an altered amino acid at position 631 and T7 RNA polymerase comprising an altered amino acid at position 639, and wherein said mutant RNA polymerase has a reduced discrimination between canonical and non-canonical nucleoside triphosphates;
   b) a primer for extending, in a template-dependent manner, a nucleic acid comprising a sequence complementary to said nucleic acid molecule;
   c) four nucleoside triphosphates; and
   d) four ddNTPs.

27. The kit of claim 26, wherein said nucleoside triphosphates are chosen from the group consisting of ATP, CTP, GTP, and UTP or rTTP and said ddNTPs are ddATP, ddCTP, ddGTP, and ddUTP or ddTTP.

28. The kit of claim 26, wherein said nucleoside triphosphates are chosen from the group consisting of dATP, dCTP, dGTP, dUTP, dTTP, 7-deaza-dGTP, dITP, 5-methyl-dCTP, 5-hydroxy-methyl-dCTP and said ddNTPs are ddATP, ddCTP, ddGTP, and ddUTP or ddTTP.

29. The kit of claim 26, wherein said nucleoside triphosphates are chosen from the group consisting of 2'-F-ATP, 2'-F-CTP, 2'-F-GTP, 2'-F-UTP, 2'-F-TTP, 2'-deaza-2'-F-GTP, 2'-F-ITP, and 5-methyl-2'-F-CTP, 5-hydroxymethyl-2'-F-CTP and said ddNTPs are ddATP, ddCTP, ddGTP, and ddUTP or ddTTP.

* * * * *

UNITED STATES PATENT AND TRADEMARK OFFICE
CERTIFICATE OF CORRECTION

PATENT NO.    : 6,107,037
DATED         : August 22, 2000
INVENTOR(S)   : Rui Sousa et al.

It is certified that error appears in the above-identified patent and that said Letters Patent is hereby corrected as shown below:

<u>Column 1,</u>
Line 2, after the title, please insert -- Statement Regarding Federally Sponsored Research or Development --
Line 3, please insert -- This invention was made with United States government support awarded to the following agency: NIH GM 52522. The United States has certain rights in this invention. --

Signed and Sealed this

First Day of July, 2003

JAMES E. ROGAN
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: Other Nucleic Acid (xi) SEQUENCE DESCRIPTION: SEQ ID NO:1:

GGGAGACCGG AAU                                                    13

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: Other Nucleic Acid (xi) SEQUENCE DESCRIPTION: SEQ ID NO:2:

CGAAATTAAT ACGACTCACT ATA                                  23

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: Other Nucleic Acid (xi) SEQUENCE DESCRIPTION: SEQ ID NO:3:

GGGGGGGGGG GACT                                                14

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:4:

GGACACGGCG AA                                                    12

(2) INFORMATION FOR SEQ ID NO:5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:5:

CCCGGGATGG AATGGAGTAT TCGCCGTGTC CATGGCTGTA AGTATCC          47